(12) United States Patent
Baker et al.

(10) Patent No.: US 11,598,718 B2
(45) Date of Patent: Mar. 7, 2023

(54) METHOD OF ANALYSING AN AQUEOUS FLUID USING 2D-IR SPECTROSCOPY

(71) Applicant: The University of York, York (GB)

(72) Inventors: Matthew Baker, Crianlarich (GB); Neil T. Hunt, York (GB); Samantha Rutherford, Glasgow (GB); Gordon Hithell, Renfrew (GB)

(73) Assignee: The University of York, York (GB)

( * ) Notice: Subject to any disclaimer, the term of this patent is extended or adjusted under 35 U.S.C. 154(b) by 0 days.

(21) Appl. No.: 16/972,345

(22) PCT Filed: Jun. 7, 2019

(86) PCT No.: PCT/GB2019/051585
§ 371 (c)(1),
(2) Date: Dec. 4, 2020

(87) PCT Pub. No.: WO2019/234443
PCT Pub. Date: Dec. 12, 2019

(65) Prior Publication Data
US 2021/0247301 A1    Aug. 12, 2021

(30) Foreign Application Priority Data

Jun. 7, 2018 (GB) .................................. 1809403

(51) Int. Cl.
*G01N 21/3577*    (2014.01)
*G01N 21/63*    (2006.01)
(Continued)

(52) U.S. Cl.
CPC ....... *G01N 21/3577* (2013.01); *G01N 21/636* (2013.01); *G01N 33/49* (2013.01); *G01N 2021/3595* (2013.01)

(58) Field of Classification Search
CPC .. G01N 21/3577; G01N 21/636; G01N 33/49; G01N 2021/3595; G01N 33/487
See application file for complete search history.

(56) References Cited

U.S. PATENT DOCUMENTS

2001/0050083 A1* 12/2001 Marchitto ........ A61B 5/150351
128/898
2013/0221222 A1* 8/2013 Baiz ..................... G01N 21/636
250/339.01

(Continued)

FOREIGN PATENT DOCUMENTS

WO    WO 2017/127679 A1    7/2017
WO    WO-2017127679 A1 *  7/2017    ............. G01N 21/35
WO    WO 2017/221027 A1   12/2017

OTHER PUBLICATIONS

Wu et al., "Two-dimensional infrared spectroscopy and principle component analysis studies of the secondary structure and kinetics of hydrogen-deuterium exchange of human serum albumin", Journal of Physical Chemistry B, vol. 105, pp. 6251-6259. (Year: 2001).*

(Continued)

*Primary Examiner* — Kiho Kim
(74) *Attorney, Agent, or Firm* — Alston & Bird LLP

(57) ABSTRACT

A method of analysing an aqueous fluid comprising obtaining a 2D-IR spectrum of a sample of the aqueous fluid using a 2D-IR spectrometer configured to apply a sequence of IR pulses to the sample, wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs.

20 Claims, 8 Drawing Sheets

(51) Int. Cl.
 G01N 33/49 (2006.01)
 G01N 21/35 (2014.01)

(56) References Cited

U.S. PATENT DOCUMENTS

2013/0314702 A1    11/2013  DeFlores et al.
2015/0211988 A1*    7/2015  Carmona Hernandez ..................
                                                        G01N 21/65
                                                        424/172.1

OTHER PUBLICATIONS

Lee et al., "2D IR spectra of cyanide in water investigated by molecular dynamics simulations", Journal of Chemical Physics, vol. 139, pp. 054506-1 to 054506-12. (Year: 2013).*

Roberts et al., "Structureal Rearrangements in Water viewed by Through Two-dimensional Spectroscopy", 2009, Accounts of Chemical Research, vol. 42, No. 9, pp. 1239-1249. (Year: 2009).*

Adamczyk, K., et al., "Ultrafast infrared spectroscopy reveals water-mediated coherent dynamics in an enzyme active site", Chemical Science, 2015, vol. 6, No. 1, pp. 505-516, UK.

Baiz, C. R., et al., "Coherent two-dimensional infrared spectroscopy: Quantitative analysis of protein secondary structure in solution", Analyst, 2012, vol. 137, No. 8, pp. 1793-1799, UK.

International Searching Authority, International Search Report and Written Opinion received for Application No. PCT/GB2019/051585, dated Sep. 18, 2019, 12 pages, European Patent Office, Netherlands.

Ishikawa, H., et al., "Neuroglobin dynamics observed with ultrafast 2D-IR vibrational echo spectroscopy", Proc. National Academy of Sciences, Oct. 9, 2007, vol. 104, No. 41, pp. 16116-16121, US.

Kraemer, D., et al., "Temperature dependence of the two-dimensional infrared spectrum of liquid $H_2O$", Proc. National Academy of Sciences, Jan. 15, 2008, vol. 105, No. 2, pp. 437-442, US.

Liu, J., et al., "Prognostic value of pretreatment albumin-globulin ratio in predicting long-term mortality in gastric cancer patients who underwent D2 resection", OncoTargets and Therapy, 2017, vol. 10, pp. 2155-2162, UK.

Park, S., et al., "Ultrafast 2D-IR vibrational echo spectroscopy: a probe of molecular dynamics", Laser Physics Letters, 2007, vol. 4, No. 10, pp. 704-718, Germany.

Adamczyk, Katrin, et al., "Measuring protein dynamics with ultrafast two-dimensional infrared spectroscopy", Meas. Sci. Technol., May 15, 2012, 17 pages, vol. 23, id. 062001, IOP Publishing, UK.

Adamczyk, Katrin, et al., "The Effect of Point Mutation on the Protein-Ligand Interactions in Equilibrium Structural Fluctuations of Myoglobin", Phys. Chem. Chem. Phys., Mar. 28, 2012, pp. 7411-7419, vol. 14, Royal Society of Chemistry, UK.

Ashihara, S., Huse, N., et al., "Vibrational couplings and ultrafast relaxation of the O—H bending mode in liquid $H_2O$", Chem. Phys. Lett., Apr. 25, 2005, pp. 66-70, vol. 424, Elsevier B. V., Netherlands.

Asplund, M. C., et al., "Two-dimensional infrared spectroscopy of peptides by phase-controlled femtosecond vibrational photon echoes", Proc. Natl Acad. Sci., Jul. 18, 2000, pp. 8219-8224, vol. 97, No. 15, PNAS, US.

Baker, Matthew, J. et al., "Developing and understanding biofluid vibrational spectroscopy: a critical review", Chem. Soc. Rev., Apr. 2016, pp. 1803-1818, vol. 45, No. 7, Royal Society of Chemistry, UK.

Bonnier, Franck, et al., "Improved protocols for vibrational spectroscopic analysis of body fluids", Journal of Biophotonics, Oct. 16, 2013, pp. 167-179, vol. 7, Nos. 3-4, Wiley-VCH Verlag GmbH & Co. KGaA, Germany.

Dahms, Fabian, et al., "Large-amplitude transfer motion of hydrated excess protons mapped by ultrafast 2D IR spectroscopy", Science, Aug. 4, 2017, pp. 491-494, vol. 357, No. 6350, American Association for the Advancement of Science, US.

De Marco, Luigi, et al., "Anharmonic exciton dynamics and energy dissipation in liquid water from two-dimensional infrared spectroscopy", J Chem Phys, Sep. 1, 2016, pp. 094501-1 to 094501-14, vol. 145, American Institute of Physics, US.

Deflores, Lauren P., et al., "Two-dimensional Fourier transform spectroscopy in the pump-probe geometry", Optics Letters, Oct. 15, 2007, pp. 2966-2968, vol. 32, No. 20, Optical Society of America, US.

Donaldson, P. M., et al., "A 100 kHz Pulse Shaping 2D-IR Spectrometer Based on Dual Yb:KGW Amplifiers", J. Phys. Chem. A, Dec. 18, 2018, pp. 780-787, vol. 122, No. 3, American Chemical Society, US.

Dunkelberger, Emily. B., et al., "Transition Dipoles from 1D and 2D Infrared Spectroscopy Help Reveal the Secondary Structures of Proteins: Application to Amyloids", J. Phys. Chem. B, Oct. 7, 2015, pp. 14065-14075, vol. 119, American Chemical Society, US.

Finkels Tein, Ilya J., et al., "Probing dynamics of complex molecular systems with ultrafast 2D-IR vibrational echo spectroscopy", Phys. Chem. Chem. Phys., Feb. 20, 2007, pp. 1533-1549, vol. 9, Royal Society of Chemistry, UK.

Fritzsch, Robby, et al., "Rapid screening of DNA-ligand complexes via 2D-IR spectroscopy and ANOVA-PCA", Analytical Chemistry, Jan. 23, 2018, pp. 2732-2740, American Chemical Society, US.

Gajjar, Ketan, et al., "Fourier-transform infrared spectroscopy coupled with a classification machine for the analysis of blood plasma or serum: a novel diagnostic approach for ovarian cancer", Analyst, Jan. 8, 2013, pp. 3917-3926, vol. 138, Royal Society of Chemistry, UK.

Greetham, Gregory M., et al., "ULTRA: A Unique Instrument for Time-Resolved Spectroscopy", Applied Spectroscopy, Nov. 12, 2010, pp. 1311-1319, vol. 64, Society for Applied Spectroscopy, SAGE Publications, Inc., US.

Greve, Christian, et al., "N-H Stretching Excitations in Adenosine-Thymidine Base Pairs in Solution: Pair Geometries, Infrared Line Shapes, and Ultrafast Vibrational Dynamics", J. Phys. Chem. A, Dec. 12, 2012, pp. 594-606, vol. 117, No. 3, American Chemical Society, US.

Grosserueschkamp, Frederik, et al., "Spatial and molecular resolution of diffuse malignant mesothelioma heterogeneity by integrating label-free FTIR imaging, laser capture microdissection and proteomics", Scientific Reports, Mar. 30, 2017, 12 pages, vol. 7, Nature Publishing Group, UK.

Hamm, Peter, et al., "Structure of the Amide I Band of Peptides Measured by Femtosecond Nonlinear-Infrared Spectroscopy", J. Phys. Chem. B, Jun. 11, 1998, pp. 6123-6138, vol. 102, American Chemical Society, US.

Hamm, Peter, et al., "The two-dimensional IR nonlinear spectroscopy of a cyclic penta-peptide in relation to its three-dimensional structure", Proc. Natl Acad. Sci., Mar. 1999, pp. 2036-2041, vol. 96, PNAS, US.

Hands, James R., et al., "Attenuated Total Reflection Fourier Transform Infrared (ATR-FTIR) spectral discrimination of brain tumour severity from serum samples", Journal of Biophotonics, Jan. 7, 2014, pp. 189-199, vol. 7, Nos. 3-4, Wiley-VCH Verlag GmbH & Co. KGaA, Germany.

Hithell, Gordon, et al., "Chapter 3: Applications of 2D-IR spectroscopy to probe the structural dynamics of DNA", Frontiers and Advances in Molecular Spectroscopy, Laane, J., Ed., Jun. 2018, pp. 77-100, Elsevier Inc., Netherlands.

Hithell, Gordon, et al., "Ultrafast 2D-IR and optical Kerr effect spectroscopy reveal the impact of duplex melting on the structural dynamics of DNA", Phys. Chem. Chem. Phys., Apr. 6, 2017, pp. 10333-10342, vol. 19, No. 16, Royal Society of Chemistry, UK.

Hu, Shen, et al., "Human body fluid proteome analysis", Proteomics, Nov. 28, 2006, pp. 6326-6353, vol. 6, No. 23, Wiley-VCH Verlag GmbH & Co. KGaA, Germany.

Hughes, Caryn, et al., "Introducing Discrete Frequency Infrared Technology for High-Throughput Biofluid Screening", Scientific Reports, Feb. 4, 2016, vol. 6, Nature Publishing Group, UK.

Kania, Ratal, et al. "Investigating the vibrational dynamics of a 17e-metallocarbonyl intermediate using ultrafast two dimensional infrared spectroscopy", Phys. Chem. Chem. Phys., Dec. 23, 2009, pp. 1051-1063, vol. 12, Royal Society of Chemistry, UK.

(56) References Cited

OTHER PUBLICATIONS

Khalil, M, et al., "Coherent 2D-IR spectroscopy: molecular structure and dynamics in solution", J. Phys. Chem. A, Jun. 19, 2003, pp. 5258-5279, vol. 107, American Chemical Society, US.

Kim, Yung Sam, et al., "Two-dimensional infrared spectroscopy of the alanine dipeptide in aqueous solution", J Phys Chem B, Mar. 19, 2005, pp. 7511-7521, vol. 109, No. 15, American Chemical Society, US.

Kim, Yung, Sam, et al., "Dynamics of amide-I modes of the alanine dipeptide in $D_2O$", J. Phys. Chem. B, Mar. 1, 2005, pp. 6884-6891, vol. 109, No. 14, American Chemical Society, US.

Kong, Kenny, et al., "Raman spectroscopy for medical diagnostics—From in-vitro biofluid assays to in-vivo cancer detection", Advanced Drug Delivery Reviews, Mar. 22, 2015, pp. 121-134, vol. 89, Elsevier B. V., Netherlands.

Koyama, Teruhide, et al., "Serum albumin to globulin ratio is related to cognitive decline via reflection of homeostasis: a nested case-control study", BMC Neurology, 2016, 10 pages, vol. 16, No. 253, Springer Nature, UK.

Krummel, Amber T., et al., "Inter and intrastrand vibrational coupling in DNA studied with heterodyned 2D-IR spectroscopy", J. Phys. Chem. B, Aug. 12, 2003, pp. 9165-9169, vol. 107, No. 35, American Chemical Society, US.

Krummel, Amber, et al., "DNA vibrational coupling revealed with two-dimensional infrared spectroscopy: Insight into why vibrational spectroscopy is sensitive to DNA structure", J. Phys. Chem. B, Jun. 22, 2006, pp. 13991-14000, vol. 110, No. 28, American Chemical Society, US.

Liu, J. J., et al., "Prognostic value of pretreatment albumin-globulin ratio in predicting long-term mortality in gastric cancer patients who underwent D2 resection", Oncotargets and Therapy, Apr. 13, 2017, pp. 2155-2162, vol. 10, Dove Press, UK.

Luther, Bradley M., et al., "2D IR spectroscopy at 100 kHz utilizing a Mid-IR OPCPA laser source", Optics Express, Feb. 19, 2016, pp. 4117-4127, vol. 24, No. 4, Optical Society of America, US.

Minnes, Lucy, et al., "Quantifying Secondary Structure Changes in Calmodulin using 2D-IR Spectroscopy", Analytical Chemistry, Sep. 18, 2017, p. 10898-10906 vol. 89, American Chemical Society, US.

Paarmann, A., et al., "Probing intermolecular couplings in liquid water with two-dimensional infrared photon echo spectroscopy", J. Chem. Phys., May 19, 2008, 6 pages, vol. 128, No. 191103, American Institute of Physics, US.

Peng, Chunte S., et al., "Anharmonic Vibrational Modes of Nucleic Acid Bases Revealed by 2D IR Spectroscopy", J. Am. Chem. Soc., Aug. 23, 2011, pp. 15650-15660, vol. 133, No. 39, American Chemical Society, US.

Peters, A. S., et al., "Serum-infrared spectroscopy is suitable for diagnosis of atherosclerosis and its clinical manifestations", Vibrational Spectroscopy, May 4, 2017, pp. 20-26, vol. 92, Elsevier B. V., Netherlands.

Petricoin, Emanual F., et al. "The blood peptidome: a higher dimension of information content for cancer biomarker discovery", Nature Reviews | Cancer, Dec. 2006, pp. 961-967, vol. 6, Nature Publishing Group, Germany.

Ramakers, Lennart A. I., et al., "2D-IR spectroscopy shows that optimized DNA minor groove binding of Hoechst33258 follows an induced fit model", J. Phys. Chem. B, Jan. 19, 2017, pp. 1295-1303, vol. 121, American Chemical Society, US.

Shaw, Daniel J., et al. "Examining the role of protein structural dynamics in drug resistance in *Mycobacterium tuberculosis*", Chemical Science, Oct. 16, 2017, pp. 8384-8399, vol. 8, Royal Society of Chemistry, UK.

Shim, Sang-Hee, et al., "Automated 2D IR Spectroscopy Using a Mid-IR Pulse Shaper and Application of this Technology to the Human Islet Amyloid Polypeptide", Proc. Nat. Acad. Sci., Sep. 4, 2007, pp. 14197-14202, vol. 104, No. 36, PNAS, US.

Shim, Sang-Hee, et al., "Automated 2D-IR spectroscopy using a mid-IR pulse shaper and application of this technology to the human islet amyloid polypeptide", Proc. Natl. Acad. Sci., Sep. 4, 2007, pp. 14197-202, vol. 104, No. 36, PNAS, US.

Shim, Sang-Hee, et al., "How to turn your pump-probe instrument into a multidimensional spectrometer: 2D-IR and Vis spectroscopies via pulse shaping", Phys. Chem. Chem. Phys., Dec. 10, 2008, pp. 748-761, vol. 11, Royal Society of Chemistry, UK.

Singh, Vipender, et al., "Direct Observation of Multiple Tautomers of Oxythiamine and their Recognition by the Thiamine Pyrophosphate Riboswitch", ACS Chem Biol, Oct. 15, 2013, pp. 227-236, vol. 9, No. 1, American Chemical Society, US.

Stewart, Andrew I., et al., "Determination of the photolysis products of [FeFe] hydrogenase enzyme model systems using ultrafast multidimensional infrared spectroscopy", Inorg. Chem., Sep. 16, 2010, pp. 9563-9573, vol. 49, No. 20, American Chemical Society, US.

Szyc, Łukasa, et al., "Ultrafast dynamics of N—H and O—H stretching excitations in hydrated DNA oligomers", Chem Phys, Aug. 23, 2008, pp. 36-44, vol. 357, Elsevier B. V., Netherlands.

Thämer, Martin, et al., "Ultrafast 2D IR spectroscopy of the excess proton in liquid water", Science, Oct. 2, 2015, pp. 78-82, vol. 350, No. 6256, American Association for the Advancement of Science, US.

The International Bureau of WIPO, International Preliminary Report on Patentability (Chapter I) received for Application No. PCT/GB2019/051585, Dec. 8, 2020, 9 pages, Switzerland.

Tracy, Kathryn M., et al., "High-Throughput Two-Dimensional Infrared (2D IR) Spectroscopy Achieved by Interfacing Microfluidic Technology with a High Repetition Rate 2D IR Spectrometer", Journal of Physical Chemistry Letters, Nov. 11, 2016, pp. 4865-4870, vol. 7, No. 23, American Chemical Society, US.

Yang, Ming, et al., "Femtosecond Two-Dimensional Infrared Spectroscopy of Adenine-Thymine Base Pairs in DNA Oligomers", J Phys Chem B, Jan. 10, 2011, pp. 1262-1267, vol. 115, No. 5, American Chemical Society, US.

Zanni, Martin, T., et al., "Solvent dependent conformational dynamics of dipeptides studied with two-dimensional infrared spectroscopy", Biophysical Journal, Feb. 18, 2001, pp. 8A-9A, vol. 80, No. 1, pt. 2, Cell Press, US.

\* cited by examiner

METHOD OF ANALYSING AN AQUEOUS FLUID USING 2D-IR SPECTROSCOPY

CROSS REFERENCE TO RELATED APPLICATIONS

This application is a National Stage Application, filed under 35 U.S.C. § 371, of International Application No. PCT/GB2019/051585, filed Jun. 7, 2019, which international application claims priority to and the benefit of Great Britain Application No. 1809403.7, filed Jun. 7, 2018; the contents of both of which as are hereby incorporated by reference in their entireties.

BACKGROUND

Related Field

The invention relates to an improved method of analysing an aqueous fluid using two dimensional infrared (2D-IR) spectroscopy. The invention extends to use of said method in a method of diagnosing or prognosing abnormal conditions in a subject.

Description of Related Art

Infrared (IR) spectroscopy is widely used in the chemical analysis of solids, liquids and gases. In a simple form, IR spectroscopy involves irradiating a sample with IR radiation to produce an absorbance spectrum which provides vibrational information characteristic of molecules in the sample. One of the problems encountered in the taking of IR spectra of aqueous liquids is the presence of absorbance peaks due to water. These can dominate the spectra, masking peaks due to other components in the liquid, thus limiting the usefulness of this analytical technique for aqueous substances.

Successful treatment of disease is often critically dependent upon obtaining an early and accurate diagnosis. Testing strategies that are free of labelling, that are based on minimally-invasive sampling methods, and that deliver results quickly and economically are desirable.

Diagnosis based on the analysis of biofluids, such as blood serum, is particularly attractive. Blood serum samples are easily obtained with minimal discomfort to the patient and can provide data from the circulatory system, which accesses virtually all parts of the body and major organs. As a result, blood serum contains a range of potentially diagnostic chemical markers including the composition of the circulatory proteome and low molecular weight peptidome as well as species such as lipids, sugars and nucleic acids[1-3].

Although blood serum is chemically-rich, the concentration ranges of molecules in serum span ten orders of magnitude (g-ng/L)[2] and this, along with the diversity of the molecules, means that accurate quantification of all the components in blood serum is practically impossible. Current analysis technologies focus on assays featuring antibody panels or mass-spectrometry measurements. Both techniques require laboratory-based testing, and assays rely on the availability of specific antibodies for proteins of interest and require significant sample preparation.

Increasingly however, information on the broad biomolecular fingerprint of metabolic function that biofluids can provide is becoming preferred to single-metabolite detection as an early warning of deteriorating patient health, due to the heterogeneous nature of disease[1-2]. For example, changes in the chemical fingerprint of biofluids have been shown to provide indicators of the presence of numerous types of cancer[2,4]. The protein content of serum has also been shown to have diagnostic relevance[5-6]. Human serum typically contains ~70 mg/ml of proteins composed of albumin (~75%) and the globulin proteins. The term globulins encompasses a large number of proteins of which the γ-globulins (IgG, IgA, IgM) are the dominant fraction by concentration. Knowledge of the ratio of albumin to globulins (AGR) is sufficient to provide important insights into general health, the presence of an inflammatory response and even an indication of the ability of the patient to survive cancer therapy[5-7]. Beyond the AGR, a more detailed breakdown of the globulin composition enables deeper insights into specific health problems, such as liver disease (indicated by changes in IgG, IgA and α-lipoprotein content) or chronic infection (IgM)[8]. Despite the importance of the AGR however, it is still obtained indirectly from the difference between the concentration of albumin and the total protein content of serum via a laboratory-based test rather than by a single direct measurement.

The application of methods such as IR absorption spectrometry or Raman scattering to serum analysis is increasing[3]. IR spectroscopic methods are widely used in the chemical analysis of solids, liquids and gases. They are fast, label-free and provide broad chemical coverage. However, water absorbs strongly across the IR spectrum and IR absorption spectra obtained for aqueous liquids can be dominated by presence of absorbance peaks due to water, resulting in the masking of peaks due to other components in the liquid. In particular, biofluids are aqueous and water absorption impairs traditional transmission measurements[3]. For example, traditional absorption measurements of the protein content of biofluids are impaired by the strong absorbance of $H_2O$ near 1650 $cm^{-1}$, which obscures the informative protein amide I absorption. This problem has been circumvented by drying the samples or H-D exchanges but this adds to sample preparation time and can make data analysis challenging. Water spectra can be obtained alongside serum spectra and subtracted, but the broad and often featureless absorption lineshapes lead to inaccuracies and uncertainties and this approach ignores the effect of interactions between protein and water. Drying or filtering samples takes time and has been linked to measurement uncertainties arising from sample processing[11], while alternate detection geometries, such as transflection, can introduce artefacts[3]. High brightness Quantum Cascade lasers allow transmission measurements in aqueous solutions, but are limited to narrow wavelength regions in a single measurement, making coverage of the biochemical fingerprint challenging[12]. Raman spectroscopies are powerful but require labelling or signal enhancement strategies for optimum performance[13]. Thus, a method of obtaining an IR absorption spectrum of an aqueous liquid which alleviates the above-mentioned problems would be desirable. Further a simple, fast spectroscopic method capable of measuring AGR without the need for serum pre-processing alongside the ability to clearly differentiate, for example, key proteins would offer a major step forwards in healthcare technology.

2D-IR has been widely used to investigate the structure and dynamics of proteins and the 2D-IR signal has been shown to be sensitive to protein secondary structure changes[14-15], vibrational coupling in macromolecular structures[16] and small molecule binding[17]. In addition, the ability of 2D-IR spectroscopy to spread the IR response of a molecule over a second frequency dimension offers the possibility of unravelling spectra of complex mixtures[18-19]. Recent advances in 2D-IR technology have enabled the measurement of spectra in a few seconds[20-23], comparable with benchtop IR absorption spectrometers, and it has been shown that 2D-IR could be used in high throughput screening applications[24]. 2D-IR spectroscopy of proteins is universally applied in deuterated solvents to avoid the intense absorption arising from the H—O—H bending vibration ($\delta_{H-O-H}$) of water that overlaps with the structurally-sensitive amide I vibrational mode of proteins (principally due to the C=O stretching motion of the peptide link, $v_{C=O}$). Such isotopic exchange methods are too expensive and time consuming to be compatible with clinical analysis of biofluids.

It is an object of the invention to provide a method of analysing aqueous liquids such as biofluids using an IR spectroscopic technique and/or a method of diagnosis or prognosis that alleviates or mitigates at least one of the above-mentioned problems. In particular, it is an object of the invention to provide an improved method of determining the relative concentrations of proteins in a biofluid, such as blood serum. More particularly, it is an object to the invention to provide a method of determining the ratio of albumin to globulins (AGR) in a biofluid such as blood serum.

BRIEF SUMMARY

According to a first aspect, the invention provides a method of analysing an aqueous fluid comprising obtaining a 2D-IR spectrum of a sample of the aqueous fluid using a 2D-IR spectrometer configured to apply a sequence of IR pulses to the sample, wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs. Thus the sequence of IR pulses can comprise a single pump pulse followed by a probe pulse and $T_w$ is the time between applying the single pump pulse and applying the probe pulse. Alternatively, the sequence of IR pulses can comprise a first pump pulse followed by a second pump pulse which is then followed by a probe pulse and $T_w$ is the time between applying the second pump pulse and applying the probe pulse.

It has been found that by applying the non-linear optical technique of 2D-IR spectroscopy in this manner, signal due to the water in the sample is suppressed. This results in spectra with better resolved peaks and enhancement of narrow spectral features, for example, when proteins are present in the aqueous fluid. This is because 2D-IR spectroscopy leads to an enhancement of narrow spectral features with strong transition dipole moments arising from, for example, the protein over broad features from more numerous but more weakly absorbing water molecules. This advance allows the "seeing" of proteins in water, where it was previously thought impossible to observe the amide I band of proteins in water (all previous work was done in $D_2O$). As a result, the method of the invention lends itself to more accurate quantitative analysis of components in an aqueous fluid. Further, the method of the invention allows spectroscopic analysis of aqueous biofluids, such as aqueous serum samples, directly in transmission mode without pre-treatment of the sample or complex post-experiment data analysis. Of particular interest is the application of the method of the invention to the quantitative analysis of biofluids and, in particular, the quantitative analysis of proteins in biofluids such as blood serum.

According to a second aspect, the invention provides a method of diagnosing and/or prognosing an abnormality in a subject comprising analysing a sample of an aqueous biofluid from the subject, wherein the method of analysing the sample of aqueous biofluid comprises obtaining a 2D-IR spectrum of a sample of the aqueous biofluid using a 2D-IR spectrometer configured to apply a sequence of IR pulses to the sample, wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs.

Thus according to the second aspect of the invention, there is provided a method of diagnosing and/or prognosing an abnormality in a subject comprising analysing a sample of the biofluid according to the method of the first aspect of the invention. The method of diagnosing and/or prognosing can further include the step of determining from the components or levels of components present, e.g. the relative levels of proteins, whether or not an abnormality is present and/or whether or not further testing of the subject is required. The method of the first aspect of the invention allows for a diagnosis based in a single spectroscopic measurement, for example a diagnosis based on the AGR of blood or blood serum.

DETAILED DESCRIPTION OF VARIOUS EMBODIMENTS

Figures 1A, 1B:
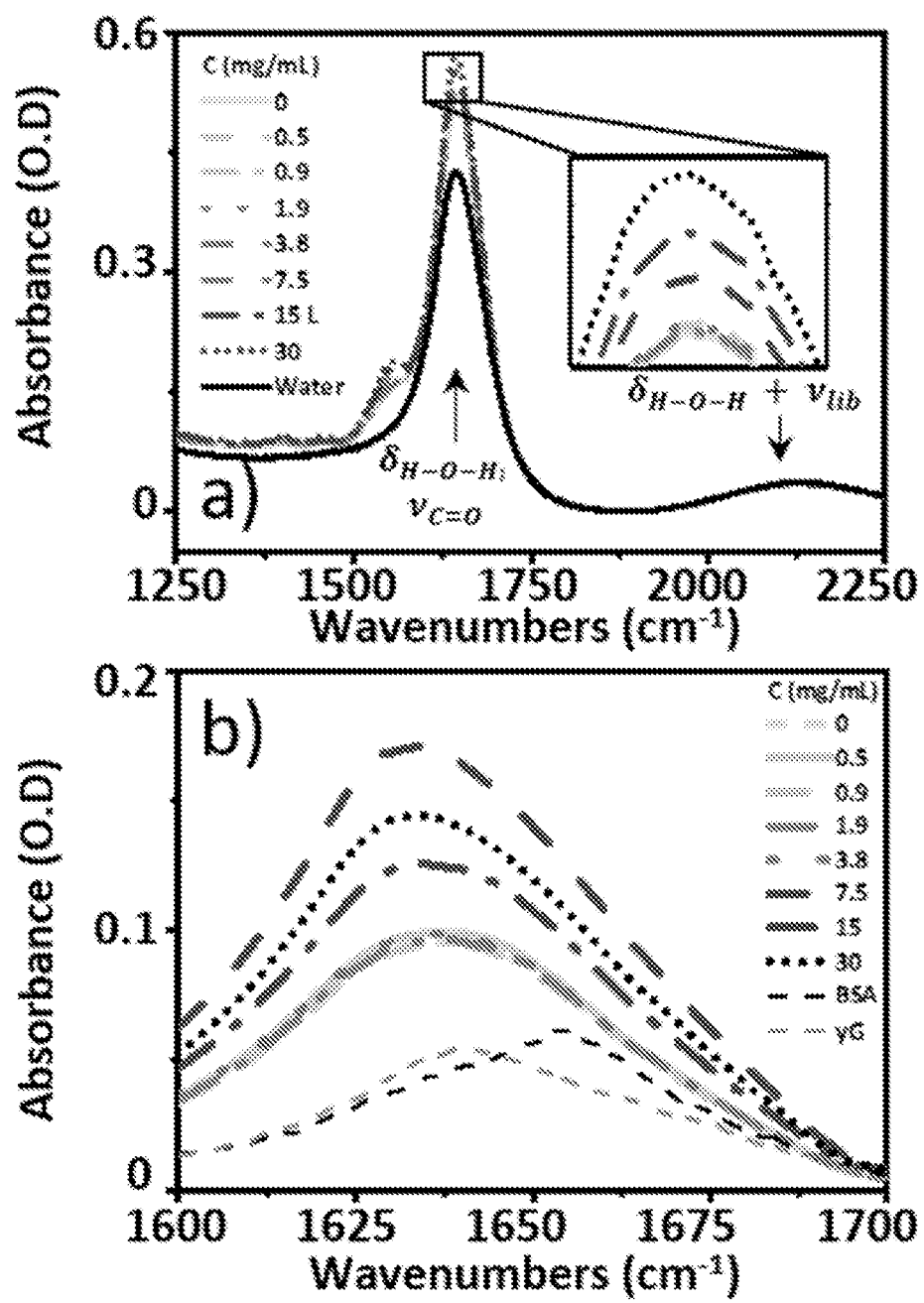
FIG. 1. (a) IR absorption spectra of horse serum samples spiked with γ-globulins. The spectrum of neat $H_2O$ is shown in black solid line. The inset shows an expansion of the tip of the peak due to the H—O—H bending mode of water and the protein amide I band at 1650 $cm^{-1}$ (b) IR absorption spectra of serum spiked with γ-globulins from a) following subtraction of the $H_2O$ spectrum.

The invention involves the use of 2D-IR spectroscopy. 2D-IR spectroscopy is a technique that is well known in the art, involving using a sequence of ultrashort infrared laser pulses to interact with the vibrational modes of a molecule. Details of this technique are given in, for example, Adamczyk K et al, "Measuring protein dynamics with ultrafast two-dimensional infrared spectroscopy", Meas. Sci. Technol. 23 (2012) 062001, for example.

2D-IR is a third-order nonlinear spectroscopy technique. Broadly, the resulting spectrum is a correlation map of excitation (pump) frequency with detection (probe) frequency and peaks in the spectrum provide information on the interaction pathways between the laser pulses and the vibrational energy levels of the system being studied.

The mid-infrared pulses are typically generated by a regeneratively amplified titanium:sapphire laser system producing pulses with a central wavelength of ~800 nm and pulse energies of ~1 mJ. The pulse repetition rate for these systems is usually 1 kHz though higher repetition rate systems can been used for 2D-IR studies [Kania R, Stewart A I, Clark I P, Greetham G M, Parker A W, Towrie M and Hunt N T 2010 Investigating the vibrational dynamics of a 17e-metallocarbonyl intermediate using ultrafast two dimensional infrared spectroscopy Phys. Chem. Chem. Phys. 12 1051-63; Stewart A I, Wright J A, Greetham G M, Kaziannis S, Santabarbara S, Towrie M, Parker A W, Pickett C J and Hunt N T 2010 Determination of the photolysis products of [FeFe] hydrogenase enzyme model systems using ultrafast multidimensional infrared spectroscopy Inorg. Chem. 49 9563-73]. The amplified pulses are used to pump white light seeded optical parametric amplifiers equipped with difference frequency mixing of the signal and idler beams in order to access the mid-IR. The output wavelength in this spectral region can generally be tuned over the range 3-15 μm (3333-667 cm$^{-1}$) with pulse energies of up to 10 μJ. Pulse durations are typically in the region of 50-100 fs giving access to spectral bandwidths of up to ~400 cm-1. The latter is particularly important for 2D-IR methods because it determines the frequency dimensions of the accessible region of the mid-IR in a single 2D spectrum.

2D-IR spectra can be obtained using a frequency domain measurement technique known as double resonance 2D-IR spectroscopy [Hamm P, Lim M and Hochstrasser R M 1998 Structure of the amide I band of peptides measured by femtosecond nonlinear-infrared spectroscopy J. Phys. Chem. B 102 6123; Hamm P, Lim M, De Grado W F and Hochstrasser R M 1999 The two-dimensional IR nonlinear spectroscopy of a cyclic penta-peptide in relation to its three-dimensional structure Proc. Natl Acad. Sci. 96 2036]. This is based upon a standard, two pulse, pump-probe type experiment and beam geometry but with the inclusion of a filtering device to reduce the bandwidth of the pump pulse to <10 cm$^{-1}$. 2D-IR spectra are obtained by scanning the pump frequency and building up a stack of narrow-bandwidth pump, broad-bandwidth probe spectra for a given pump-probe time delay. Thus in this measurement technique, the pump process is single IR pump pulse and the waiting time $T_w$ is the time between applying the single pump pulse and applying the probe pulse.

Alternatively the time domain interferometric method of acquiring 2D-IR spectra based on photon echo generation which utilizes only broad bandwidth pulses to facilitate increased spectral and temporal resolution can be used [Asplund M C, Zanni M T and Hochstrasser R M 2000 Two-dimensional infrared spectroscopy of peptides by phase-controlled femtosecond vibrational photon echoes Proc. Natl Acad. Sci. 97 8219-24]. In a photon echo experiment, three laser pulses with controllable time delays between them are used to generate the signal. The delay time between the first two pulses is labelled r, and that between pulses 2 and 3, known as the waiting time, is denoted $T_w$. In a typical 2D-IR experiment, $T_w$ is fixed while τ is scanned. The effect of the three pulses on the sample is as follows: the first pulse generates a coherent superposition of the ground and first excited vibrational states of the target vibration. This oscillates at the frequency of the transition and initially all excited molecules are in phase with each other. As time proceeds, small variations in the frequency of vibration across the ensemble of molecules result in a dephasing of the initial coherence and the rapid (ps) free induction decay of the macroscopic polarization created by the first pulse. After time r, pulse 2 changes the original superposition state into a population state, which may be of the ground or first excited state and the waiting period begins. During this period vibrational dynamics such as population relaxation and population transfer can occur from vibrationally excited states and spectral diffusion or chemical exchange processes can be observed. The waiting time can be equated with the pump-probe delay time of the double resonance experiment and it is typical for 2D-IR spectra to be recorded over a range of waiting times in order to observe these dynamic processes. Finally, after a time $T_w$, the third pulse is incident on the sample. This returns the system to a superposition of two vibrational states. The exact nature of the superposition and the component states will depend upon whether the population state was in the ground or excited state. This variation in the pathway of the three pulse interactions results in a large number of peaks being observed in the 2D-IR spectrum [Khalil M, Demirdoven N and Tokmakoff A 2003 Coherent 2D-IR spectroscopy: molecular structure and dynamics in solution *J. Phys. Chem.* A 107 5258-79; Hamm P and Zanni M T 2011 *Concepts and Method of 2D Infrared Spectroscopy* (Cambridge: Cambridge University Press)]. Following the third pulse a rephasing process occurs and after a time comparable to the delay between the first and second pulses (i.e. t~τ), a coherence is recovered and the macroscopic polarization leads to production of an echo pulse. Depending upon the component states this coherence may be at the same frequency as the initial excitation frequency (diagonal peak) or at a different frequency (off-diagonal peak), and the 2D plot shows a map of all pathways by correlating the excitation (initial coherence) frequency with detection (second coherence) frequencies [Khalil M, Demirdoven N and Tokmakoff A 2003 Coherent 2D-IR spectroscopy: molecular structure and dynamics in solution *J. Phys. Chem.* A 107 5258-79; Asplund M C, Zanni M T and Hochstrasser R M 2000 Two-dimensional infrared spectroscopy of peptides by phase-controlled femtosecond vibrational photon echoes *Proc. Natl Acad. Sci.* 97 8219-24; Finkelstein I J, Zheng J R, Ishikawa H, Kim S, Kwak K and Fayer M D 2007 Probing dynamics of complex molecular systems with ultrafast 2D-IR vibrational echo spectroscopy *Phys. Chem. Chem. Phys.* 9 1533-49]. Acquiring, or measuring, the echo signal is achieved using one of two beam geometries to create a heterodyne detection method. The application of heterodyne detection, while not strictly necessary, is beneficial for two reasons. In addition to amplifying the signal, heterodyning means that phase and sign information relating to the signal field is retained. The first beam geometry, the boxcar method, typically places the input pulses at three corners of a square arrangement [Khalil M, Demirdoven N and Tokmakoff A 2003 Coherent 2D-IR spectroscopy: molecular structure and dynamics in solution *J. Phys. Chem.* A 107 5258-79; Asplund M C, Zanni M T and Hochstrasser R M 2000 Two-dimensional infrared spectroscopy of peptides by phase-controlled femtosecond vibrational photon echoes *Proc. Natl Acad. Sci.* 97 8219-24]. These are focused and overlapped in the sample leading to emission of the echo in the phase matched direction towards the fourth corner. This has the advantage of being a zero background measurement but to achieve heterodyne detection it is necessary to overlap the signal field collinearly with a fourth, local oscillator pulse before the two beams are directed into a spectrometer and detector combination for frequency resolved detection. The latter dispersion process gives the detection frequency axis of the spectrum. The full 2D-IR spectrum is obtained by recording the interferogram of the echoflocal oscillator combination in this way as a function of τ for fixed T. Fourier transformation of this time domain signal then yields the second, excitation, frequency axis of the spectrum [Khalil M, Demirdoven N and Tokmakoff A 2003 Coherent 2D-IR spectroscopy: molecular structure and dynamics in solution *J. Phys. Chem.* A 107 5258-79]. While extremely effective, the boxcar approach does require a complex post experimental data processing procedure. The signals acquired in this manner contain contributions from laser-matter interaction pathways that do not result in an echo pulse being emitted, so-called nonrephasing pathways. In order to account for these additional contributions and to produce the desired absorptive 2D-IR lineshapes, experiments must also be carried out with pulses 1 and 2 reversed in terms of time of arrival and the two spectra summed such that the non-rephasing pathway signals cancel out [Khalil M, Demirdoven N and Tokmakoff A 2003 Coherent 2D-IR spectroscopy: molecular structure and dynamics in solution *J. Phys. Chem.* A 107 5258-79; Finkelstein I J, Zheng J R, Ishikawa H, Kim S, Kwak K and Fayer M D 2007 Probing dynamics of complex molecular systems with ultrafast 2D-IR vibrational echo spectroscopy *Phys. Chem. Chem. Phys.* 9 1533-49]. Finally, as the absolute phase of the pulses cannot be known, a technique to set the phase of the spectrum has to be applied. This is achieved using the projection slice theorem, which compares the projection of the 2D-IR spectrum onto the detection axis to a broad band pump-probe signal. This is described in more detail in [Khalil M, Demirdoven N and Tokmakoff A 2003 Coherent 2D-IR spectroscopy: molecular structure and dynamics in solution *J. Phys. Chem.* A 107 5258-79, Finkelstein I J, Zheng J R, Ishikawa H, Kim S, Kwak K and Fayer M D 2007 Probing dynamics of complex molecular systems with ultrafast 2D-IR vibrational echo spectroscopy *Phys. Chem. Chem. Phys.* 9 1533-49]. In this measurement technique, i.e. time domain interferometric method of acquiring 2D-IR spectra based on photon echo generation, the pump process is sequence of first and second IR pump pulses and the waiting time $T_w$ is the time between applying the second pulse and applying the probe pulse. A fourth pulse is employed and this is an external oscillator for heterodyne detection.

The 2D-IR spectrometer can use a pseudo pump-probe beam geometry in which the pump pulse is split into two equal intensity pulses that act as the first and second pulses respectively. These are directed into the sample collinearly and overlapped with the third 'probe' pulse in the sample [Deflores L P, Nicodemus R A and Tokmakoff A 2007 Photon Echo 2DIR in pump probe geometry *Opt. Lett.* 32 2966]. In this case a fourth local oscillator pulse is not required as the signal is emitted collinearly with the probe beam and the residual probe light acts as a local oscillator. An additional advantage is that, once detected and Fourier transformed, the 2D signal produced automatically compensates for the nonrephasing pathways, providing correctly phased absorptive spectra in a more straightforward manner. An alternative approach to this technique incorporates a mid-IR pulse shaping device to produce the two pump pulses [Shim S H, Strasfeld D B, Ling Y L and Zanni M T 2007 Automated 2D-IR spectroscopy using a mid-IR pulse shaperand application of this technology to the human islet amyloid polypeptide *Proc. Natl Acad. Sci.* 104 14197-202; Shim S H and Zanni M T 2009 How to turn your pump-probe instrument into a multidimensional spectrometer: 2D-IR and Vis spectroscopies via pulse shaping *Phys. Chem. Chem. Phys.* 11 748-61] in place of an adapted Michelson-type interferometer [Deflores L P, Nicodemus R A and Tokmakoff A 2007 Photon Echo 2DIR in pump probe geometry *Opt. Lett.* 32 2966]. The advantage of accurately knowing the temporal separation and relative phase of the two pulses that arises from implementation of the pulse shaper further simplifies the production of 2D-IR spectra while the ability to control the relative pump pulse phases leads to applications such as phase cycling, which can be used to reduce problems due to scattered light when obtaining spectra from optically heterogeneous samples such as proteins or other biological systems. The installation and use of a pulse shaper has been described in detail in Shim S H and Zanni M T 2009 How to turn your pump-probe instrument into a multidimensional spectrometer: 2D-IR and Vis spectroscopies via pulse shaping *Phys. Chem. Chem. Phys.* 11 748-61. Thus in this measurement technique, the pump process is sequence of first and second IR pump pulses and the waiting time $T_w$ is the time between applying the second pulse and applying the probe pulse.

In a first aspect, the invention provides a method of analysing an aqueous fluid comprising obtaining a 2D-IR spectrum of a sample of the aqueous fluid using a 2D-IR spectrometer configured to apply a sequence of IR pulses to the sample, wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs. Thus the sequence of IR pulses can comprise a single pump pulse followed by a probe pulse and $T_w$ is the time between applying the single pump pulse and applying the probe pulse. Alternatively, the sequence of IR pulses can comprise first and second pump pulses followed by a probe pulse and $T_w$ is the time between applying the second pump pulse and applying the probe pulse.

The invention is based in part on the discovery that the relaxation timescale of $\delta_{H-O-H}$ vibrational mode of water, along with the fact that 2D-IR spectral signatures scale with the fourth power of the transition dipole moment, can be used to extract the signal of proteins, for example, from that of the water in a single 2D-IR spectrum of an aqueous fluid, without complex spectral post-processing. The vibrational relaxation of the bleach of the $\delta_{H-O-H}$ mode of water at 1650 cm$^{-1}$ occurs on a ~220 fs timescale. Thus, the waiting time ($T_w$) of 150 to 350 fs at which the 2D-IR spectra are obtained in the method of the invention corresponds to a minimum in the water signal. Thus the waiting time allows further controlled separation of the 2D-IR signal from that of the background water signal. The pulses are of very short duration and are typically Gaussian in temporal profile. In practice $T_w$ is measured from the peak intensity/electric field of one pulse to the peak of the next. $T_w$ is from 150 to 350 fs and can be from 200 to 300 fs, 230 to 270 fs or 240 to 260 fs. Preferably $T_w$ is 250 fs.

The aqueous fluid can be any aqueous fluid and includes aqueous biofluids such as blood, blood serum, urine, cerebrospinal fluid, faeces, bile, breast milk, ejaculate, mucus, saliva, vitreous humour, tears, sweat, lymph, amniotic fluid, vaginal secretion and the like. By aqueous means the fluid comprises water ($H_2O$). Biofluids are bodily fluids and these can be mammalian, human and/or animal in origin. The aqueous fluid may comprise water and one or more components such as a pharmaceutically active chemical compound, proteins, amino acids, peptides. Preferably the aqueous fluid does not comprise $D_2O$.

The 2D-IR spectrometer is configured to apply a sequence of IR pulses to the sample, wherein the sequence comprises a pump process which is followed by a probe pulse.

The sequence of IR pulses can comprise a single pump pulse followed by a probe pulse and $T_w$ is the time between applying the single pump pulse and applying the probe pulse. Alternatively, the sequence of IR pulses can comprise first and second pump pulses followed by a probe pulse and $T_w$ is the time between applying the second pump pulse and applying the probe pulse.

The sequence of IR pulses can be 2, 3 or 4 IR pulses, and in each case, the sequence of IR pulses will comprise a pump process followed by a probe pulse and $T_w$ is the time between applying the pump pulse which precedes the probe pulse and applying the probe pulse.

The 2D-IR spectrometer can be configured to apply a sequence of three IR pulses to the sample, wherein the first and second pulses are the pump process and the third pulse is the probe pulse, and the waiting time $T_w$ is the time between applying the second pulse and applying the third pulse. In this configuration, the second pulse is the second pump pulse which is followed by the probe pulse (third pulse).

The 2D-IR spectrometer can be configured to apply a sequence of two, i.e. first and second, IR pulses to the sample, wherein the first pulse is the pump process, the second pulse is a probe pulse, and the waiting time $T_w$ is the time between applying the first pulse and applying the second pulse. In this configuration, the first pulse is the single pump pulse which is followed by the probe pulse (second pulse).

The 2D-IR spectrometer can be configured to apply a sequence of four (first, second, third and fourth) IR pulses to the sample, wherein the first and second pulses are the pump process and the third pulse is the probe pulse, and the waiting time $T_w$ is the time between applying the second pulse and applying the third pulse. The fourth pulse is an external oscillator for heterodyne detection. In this configuration, the second pulse is the second pump pulse which is followed by the probe pulse (third pulse).

The duration of the pulses can be from 50 to 300 fs and, preferably the duration of the pulses is 50 fs.

The spectrometer is configured to apply a pump process to the sample. The pump process is also known as the excitation event.

Typically, the frequency of the pump pulse or pulses is centred at 1650 cm$^{-1}$ and the band width is from 100 cm$^{-1}$ to 450 cm$^{-1}$.

Typically, the frequency and band width of the probe pulse is the same as the pump pulse. The same laser source can be used for the pump pulse(s) and the probe pulse.

The polarisation of the pump and probe beams can be parallel polarisation or perpendicular polarisation. Parallel polarisation is preferred as perpendicular polarisation tends to reduce the signal strength.

The path length of the radiation through the sample can be relatively short, for example from 2.5 to 6 microns, 2.5 to 3.5 microns or 3 microns, to help avoid saturation of the water peak in the spectrum.

A 2D-IR spectrum is a correlation map of excitation (pump) with detection (probe) frequency. The map or plot shows that if a vibrational mode of a molecule is excited at a particular pump frequency, then after an amount of time determined by $T_w$, peaks in the spectrum identify other modes of the molecule that are influenced in some way by this excitation. The pump frequency is the frequency of the initial excitation event and relates to the frequency of the pump pulses. A pump slice is a cross section through a 2D-IR spectrum at affixed pump frequency. Peaks in the spectrum provide information on the interaction pathways between the laser pulses and the vibrational energy levels of the system being studied.

By method of analysing an aqueous fluid includes a method of identifying a component or components in the aqueous fluid. The presence of a peak in the 2D-IR spectrum indicates that the aqueous fluid contains a component other than water.

The method of the first aspect of the invention may further comprise identifying a peak or peaks in the 2D-IR spectrum by comparing the 2D-IR spectrum to a reference 2D-IR spectrum. The reference 2D-IR spectrum can be of a known molecule or compound, for example a protein such as albumin, or it can be of a group of molecules or compounds that are structurally related, for example, proteins such as γ-globulins. The terms albumin and albumins are used herein interchangeably. The terms globulin and globulins are used herein interchangeably. The 2D-IR spectrum of the reference sample should be taken under as near as possible identical conditions to that of the sample.

The method of the first aspect of the invention may further comprise determining the presence (or the absence) of one or more: proteins such as albumins, globulins and myoglobin; peptides; DNA; RNA; and/or amino acids such as glycine in the aqueous fluid. Thus the method may further comprise determining whether or not any: proteins such as albumins, globulins and myoglobin; peptides; DNA; RNA; and/or amino acids such as glycine are present in the aqueous fluid. The method is particularly effective for detection of proteins as they have their own unique 2D spectral signature.

The 2D-IR peak at pump frequency for γ-globulins is 1639 $cm^{-1}$ and the 2D-1R peak at pump frequency for albumin is 1656 $cm^{-1}$. Thus in one embodiment, the method of the first aspect of the invention involves determining if albumin is present in the aqueous fluid by determining if the spectrum comprises a peak at a frequency of 1656 $cm^{-1}$ and/or determining if γ-globulins are present in the aqueous fluid by determining if the spectrum has a peak at a frequency of 1639 $cm^{-1}$.

In another embodiment, when the 2D-IR spectrum comprises a peak or peaks, the method of the first aspect of the invention comprises identifying at least one peak and quantifying the at least one peak using a calibration based on one or more reference 2D-IR spectra. The one or more reference 2D-IR spectra are of aqueous fluids containing of known concentrations of the substance identified as causing the at least one peak. The one or more reference 2D-IR spectra should be taken using the same or a similar 2D-IR spectrometer.

In another embodiment of the method of the first aspect of the invention, the method comprises determining a ratio of albumin to globulins present in the sample. Where the 2D-IR spectrum contains peaks due to albumin and γ-globulins, the method comprises determining a ratio of albumin to γ-globulins present in the sample. When the aqueous sample comprises or is blood serum, the amount of γ-globulins (IgG, IgA, IgM) can be used as being representative of the amount of globulins in the blood serum. The γ-globulins are the dominant fraction by concentration of globulins in blood serum.

In another embodiment of the first aspect of the invention, wherein the 2D-IR spectrum comprises a peak due to albumin (the albumin peak) and a peak due to γ-globulins (the γ-globulins peak), the method comprises determining a ratio of albumin to γ-globulins by measuring a peak height of the albumin peak (the albumin peak height) and a peak height of the γ-globulins peak (the γ-globulins peak height) and dividing the peak height of the albumin peak by the peak height of the γ-globulins peak multiplied by 1.8. In other words, the albumin to γ-globulins ratio is obtained by multiplying the γ-globulin peak height by 1.8 to obtain an adjusted γ-globulin peak height and dividing the albumin peak height by the scaled γ-globulins peak height.

In a second aspect, the invention provides a method of diagnosing and/or prognosing an abnormality in a subject comprising analysing a sample of an aqueous biofluid from the subject using the method of the first aspect of the invention, including its embodiments as described above wherein the aqueous fluid is an aqueous body fluid.

Thus the invention provides a method of diagnosing and/or prognosing an abnormality in a subject comprising analysing a sample of aqueous biofluid from the subject, wherein the method of analysing the aqueous biofluid comprises obtaining a 2D-IR spectrum of a sample of the aqueous biofluid using a 2D-IR spectrometer configured to apply a sequence of IR pulses to the sample, wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs.

The method of diagnosing and/or prognosing is ex vivo.

The subject may be mammalian, human or animal.

The method of the second aspect of the invention may comprise obtaining a sample of an aqueous biofluid from the subject. The sample may be previously obtained from the subject.

In one embodiment, the method of the second aspect of the invention does not comprise a method of surgery carried out on a human or animal body.

The method of the second aspect of the invention may further comprise determining from the 2D-IR spectrum whether treatment of the subject or further testing of the subject is required.

In one embodiment of the method of the second aspect of the invention, the abnormality is poor general health or the presence of an inflammatory response, and the method involves determining the ratio of albumin to globulins or γ-globulins in the aqueous biofluid.

In the method of the second aspect of the invention, the 2D-IR spectrum can be compared to a plurality of pre-correlated spectra stored in a database in order to derive a correlation with a favourable or unfavourable diagnosis or wherein the spectrum is correlated with a favourable or unfavourable diagnosis based on a predictive model developed by "training" a database of pre-correlated analyses. The pre-correlated spectra are 2D-IR spectra previously obtained from samples from subjects with known abnormalities. Such comparison can be carried out using pattern recognition software and/or machine learning analysis known in the art.

The advantages of the method of the invention are discussed below in relation to the following non-limiting examples.

EXAMPLES

Materials and Methods
Sample Preparation:

Pooled equine serum, serum albumin (bovine), γ-globulins (bovine) and glycine were obtained from Sigma Aldrich and used without further purification. Measurements of albumin and the globulins individually were performed using TRIS buffer (pH=7.5) to mimic the pH of the pooled serum samples. To study the spectroscopy of serum samples at a range of AGR values, γ-globulin was spiked into pooled horse serum at concentrations of 30, 15, 7.5, 3.8, 1.9, 0.9 and 0.5 mg/ml. This yields a total of 8 samples (seven spiked serum samples and one pure serum sample). Glycine was spiked in pure horse serum at concentrations ranging from 0.25 to 100 mg/ml. A reference sample containing pure water was also prepared.

To measure IR spectra using transmission mode the sample thickness was carefully controlled to avoid saturation of the $\delta_{H-O-H}$ mode of water at 1650 cm$^{-1}$. Samples were housed between two CaF$_2$ windows. No spacer was used, but the tightness of the sample holder was adjusted to obtain approximately consistent absorbance values of ~0.1 OD (optical density) for the $\delta_{OH}+v_{libr}$ combination mode of water located at 2130 cm$^{-1}$. Based upon the measured molar extinction coefficient of water, this corresponded to a sample thickness of ~2.75 μm. 2D-IR measurements were taken within 30 minutes of cell preparation, where cell preparation is the placement of the sample between the CaF$_2$ windows.

IR Spectroscopy:

IR absorption spectra were taken using a Thermo Scientific Nicolet iS10 Fourier Transform spectrometer. Spectra were the result of 20 co-added scans at a resolution of 1 cm$^{-1}$ in the spectral region 400-4000 cm$^{-1}$. A background spectrum was taken before each sample and subtracted following scaling of both to the amplitude of the $\delta_{OH}+v_{libr}$ mode.

Fourier Transform 2D-IR Spectroscopy:

Two-dimensional infrared spectra were measured using the Fourier transform methodology in a pseudo pump-probe geometry that has been described elsewhere[44]. Briefly, the ULTRA laser system[45], consisting of an amplified Ti:Sapphire laser system, produced ultrashort duration pulses (800 nm, <50 fs, 10 kHz) that were used to pump a white light seeded optical parametric amplifier (OPA). Difference frequency mixing of signal and idler from the OPA yielded mid infrared pulses of 2 mJ of energy with a bandwidth of ~400 cm$^{-1}$ centred near 1650 cm$^{-1}$. This IR beam was split using a wedged ZnSe window to produce two low intensity beams that were used as probe and reference beams (~8%). The remaining infrared light was directed into a Michelson-type interferometer to generate two 'pump' pulses with variable time-delay between them before these were recombined collinearly and focused into the sample to overlap with the probe beam. The interpulse timings (denoted T between the two pump pulses and the waiting time, T$_w$, between the second pump and probe pulses) were controlled using optical delay lines. All beams were polarized parallel with respect to each other. The three pulses led to emission of a signal in the direction of the residual probe beam. The latter acted as a local oscillator for heterodyne detection. The signal was recorded as a function of T for a fixed T$_w$ of 250 fs using a spectrometer and 128 channel mercury-cadmium-telluride (MCT) detector array combination to provide the probe frequency axis of the 2D-IR spectrum. For normalisation purposes, the reference beam was also spectrally dispersed and imaged onto a 64 channel MCT detector array. To remove the contribution of one pump-probe signal, the static arm of the interferometer was chopped at 5 kHz and consecutive shots were subtracted. The resulting spectral resolution was 2 cm$^{-1}$. The other pump-probe signal was removed by Fourier Transformation along T to yield the pump frequency axis of the 2D-IR spectrum. In order to locate time zero between the pump pulse-pair the field autocorrelation was measured using the residual pulse pair from the interferometer on a single channel MCT detector.

2D-IR Data Analysis:

All 2D-IR spectral processing and analysis was carried out using a custom made script on the statistical analysis software programme, R[46]. Prior to the analysis described in the text to obtain the AGR values, a 2$^{nd}$ order polynomial baseline subtraction was performed.

Three methods were used to obtain the AGR from the 2D spectra: i) the 2D-IR spectrum diagonal, ii) pump-frequency slices and iii) Singular Value Decomposition.

i) 2D-IR spectrum diagonal: the diagonal of each 2D spectrum was extracted, showing two distinct peaks at 1656 cm$^{-1}$ and 1639 cm$^{-1}$, which were assigned to the albumin and globulin fractions respectively. The ratio of the absolute values of the peak amplitudes of these features was used to determine the AGR following scaling of the globulin amplitude by a factor of 1.8.

ii) The pump-slice method utilised slices through the 2D-IR spectrum at 1656 cm$^{-1}$ and 1639 cm$^{-1}$, assigned to peaks of the albumin and globulin signals respectively. The ratio of the absolute values of the maximum amplitudes (heights) of the globulin pump slice, at a probe frequency of 1639 cm$^{-1}$, and that of the albumin slice at 1656 cm$^{-1}$ was used to determine the AGR following application of the scaling factor (1.8) to the globulin signal.

iii) SVD: All 2D-IR spectra were normalised to the albumin peak at 1656 cm$^{-1}$. SVD analysis fitted the serum 2D-IR spectrum to the linear sum of the independent 2D-IR spectra of albumin and globulins. The coefficients for the relative contribution of the two protein spectra were then used to give the AGR, following scaling of the globulin fraction by 1.8.

Principal component analysis (PCA) was performed using a custom made script in the statistical programme R[46]. The 2D-IR spectra were vector normalised (rescales each spectrum to have sum of squares equal to one) prior to the PCA to minimise errors from sample thickness and laser fluctuations.

Results

IR Absorption Spectroscopy:

The transmission-mode infrared absorption spectra of the samples of neat (pure) horse serum and horse serum spiked with differing concentrations of γ-globulins are dominated in the 1250-2250 cm$^{-1}$ region by a broad absorption located at 1650 cm$^{-1}$ (FIG. 1(a)). Comparison with the spectrum of neat H$_2$O (FIG. 1(a), black) shows that this feature is assignable to overlapping contributions arising from both $\delta_{H-O-H}$ mode of water and the amide I mode of the protein component of the serum sample. The use of a very short (~3 μm) path length for the samples limited the absorbance at 1650 cm$^{-1}$ to <0.6 to avoid effects due to saturation of this peak. By scaling the absorption spectra of the serum samples and water to the amplitude of the combination band of the $\delta_{H-O-H}$ mode and librational modes of water ($\delta_{H-O-H}+v_{lib}$) located at 2130 cm$^{-1}$, subtraction of the water background from the serum spectra was carried out in an attempt to reveal the spectrum of the protein content of the serum samples (FIG. 1(b)). The amide I band obtained from the serum samples was largely featureless, but gained in amplitude as the added quantity of γ-globulins increased (FIG. 1(b)).

In these experiments, it is assumed that the γ-globulins (IgG, IgA, IgM) constitute the bulk of the serum globulin fraction is made. This is believed to be a reasonable first approximation given the typically low sensitivity of IR spectroscopy to minor components of mixtures. Comparison of the water-subtracted IR absorption spectra of the serum samples with those of the serum albumin and γ-globulin protein components (dashed lines FIG. 1(b)), indicated that the amide I absorption lineshape below 1650 cm$^{-1}$ has a greater contribution from the γ-globulin proteins while the lineshape above 1650 cm$^{-1}$ has a larger contribution from albumin, but the strong overlap of the amide I absorptions prevents quantitative determination of the AGR.

Figures 2A, 2B, 2C, 2D, 2E:
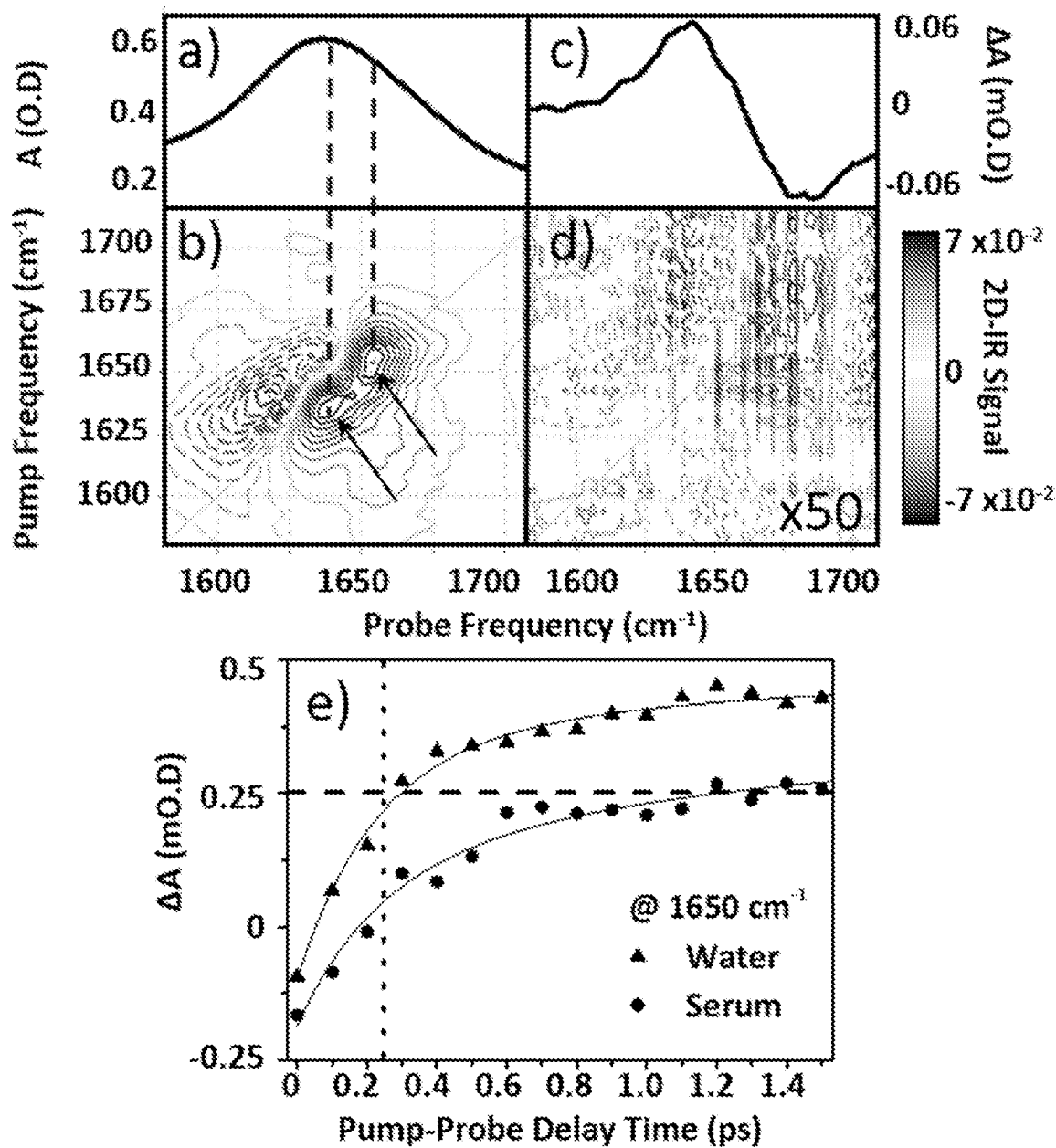
FIG. 2. (a) IR absorption spectrum of neat horse serum in the amide I region. (b) 2D-IR spectrum of the amide I region of neat serum. Arrows identify two components of the v=0-1 transition discussed in the text. (c) IR pump-probe spectrum of $H_2O$ at a pump-probe time delay of 300 fs. (d) 2D-IR spectrum of $H_2O$, magnified 50×. The 2D-IR spectra in (b) and (d) are plotted on the same scale, negative contours are dashed. (e) Temporal variation of the bleach signal observed in IR pump-probe spectra of $H_2O$ (triangles) and horse serum (circles) located at a frequency of 1650 $cm^{-1}$. Solid lines show fits to the data using a single exponential function with a decay time constant of 220 fs ($H_2O$) and 1.1 ps (serum) respectively.

2D-IR Spectroscopy:

The 2D-IR spectrum of a neat horse serum sample obtained at a waiting time of 250 fs (FIG. 2(b)) showed considerably more spectral structure than the IR absorption spectrum (FIG. 2(a)). A negative peak (solid contours) located on the diagonal of the spectrum near 1650 cm$^{-1}$ is assigned to v=0-1 transitions of modes observed in the IR absorption spectrum and clearly contains two distinct contributions with pump frequencies of 1639 and 1656 cm$^{-1}$ respectively (arrows). Positive (dashed contours) peaks due to the accompanying v=1-2 transitions are shifted to lower probe frequencies.

Comparison of the serum 2D-IR spectrum with a 2D-IR spectrum of neat water obtained under the same conditions (FIG. 2(d)) shows that the 2D-IR signal of water is significantly weaker than that of the serum. Though weak, the 2D-IR response of water was found to be in good agreement with the corresponding IR pump-probe spectrum (FIG. 2(c)) where the characteristic bleach of the v=0-1 transition of the $\delta_{H-O-H}$ mode at 1650 cm$^{-1}$ is visible along with positive features due to a combination of vibrational excitation and the weak onset of sample heating, consistent with previous observations[30].

The large discrepancy in the amplitudes of the signals obtained from serum and water suggests that the 2D-IR response of the protein is dominant in the serum spectrum, despite the large absorbance of the $\delta_{H-O-H}$ mode of water visible in the IR absorption spectrum at 1650 cm$^{-1}$. The suppression of the water background by 2D-IR is largely due to the dependence of the 2D-IR spectrum upon the 4$^{th}$ power of the vibrational transition dipole moment, leading to enhancement of the strong amide I mode of the biological macromolecules over the more plentiful, but more weakly-absorbing, water molecules[16]. The dominance of the signal due to the protein content in FIG. 2(b&d) is also enhanced by the differing waiting time dependences of the amplitudes of the 2D-IR signals from water and proteins. The results of IR pump-probe measurements (FIG. 2(e)) show that the vibrational relaxation of the bleach of the $\delta_{H-O-H}$ mode of water at 1650 cm$^{-1}$ occurs on a ~220 fs timescale, in agreement with previous measurements[30], while that of the protein amide I mode relaxes more slowly (1100 fs). Thus, the waiting time of 250 fs at which the 2D-IR spectra (FIG. 2(b&d)) were obtained corresponds to the minimum in the water signal prior to the onset of a rising signal due to water heating (FIG. 2(e)), meaning that the waiting time of the 2D-IR signal allows further controlled separation of the protein response from that of the background water signal.

Figures 3A, 3B, 3C, 3D, 3E:
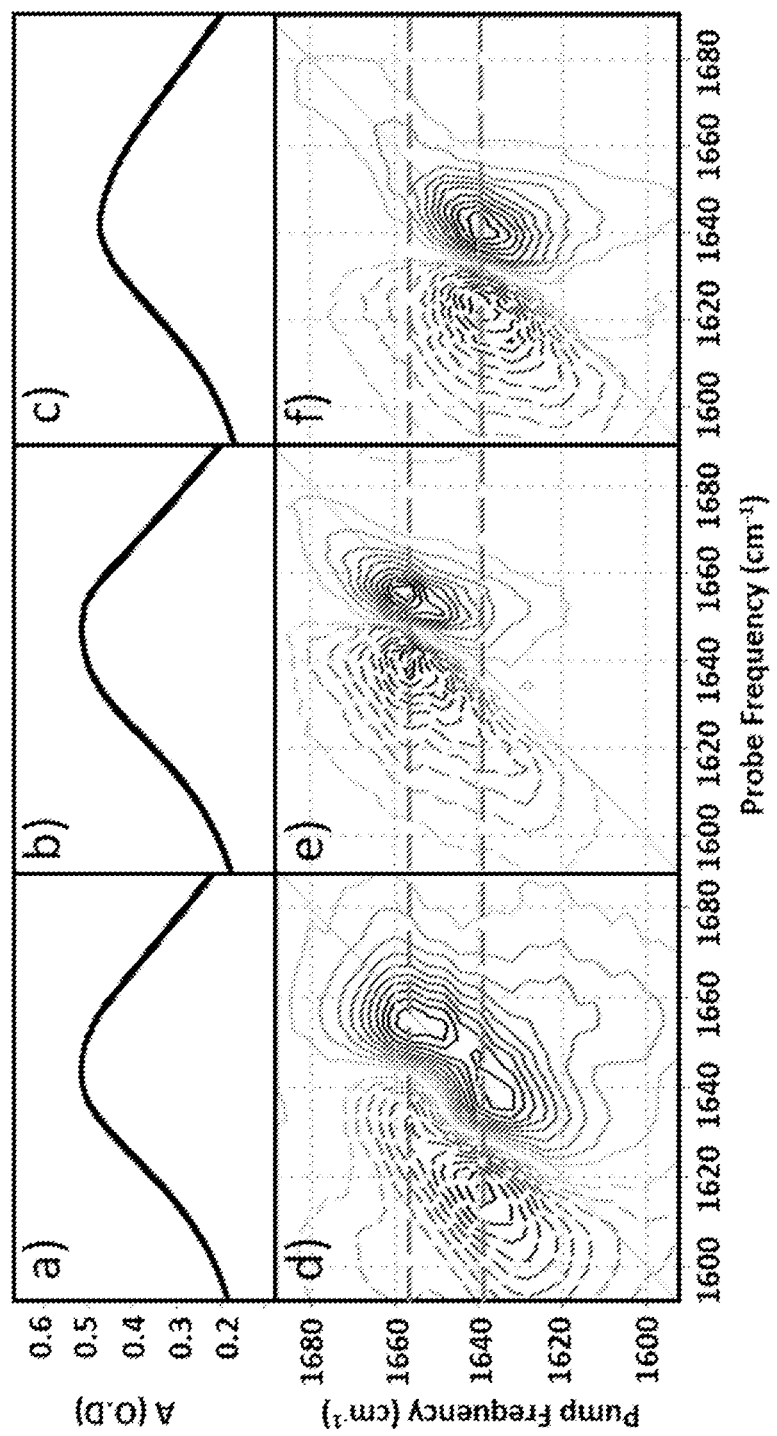
FIG. 3. IR absorption spectra of (a) neat horse serum (b) bovine serum albumin protein (c) γ-globulins (bovine). 2D-IR spectra of (d) neat horse serum (e) bovine serum albumin (f) γ-globulins (bovine). Dashed grey horizontal lines identify the peak positions of albumin and γ-globulin proteins discussed in the text. All 2D-IR spectra are plotted on the same scale, negative contours are shown in solid lines and positive contours are dashed.

The assignment of the two peaks at 1639 and 1656 cm$^{-1}$ visible in the 2D-IR spectrum of neat horse serum can be made with reference to the individual 2D-IR spectra of bovine serum albumin and γ-globulins (bovine) (FIG. 3). Here it can be seen that the peak at a pump frequency of 1639 cm$^{-1}$ can be attributed to the γ-globulin component, while that at 1656 cm$^{-1}$ is assigned to the albumin fraction. The difference in frequency of the two protein signals arises from the fact that the secondary structure of serum albumin is largely α-helical, while the globulins have a higher proportion of β-sheet, which shifts the centre of mass of the amide I band to lower frequency.

The fact that these peaks are separable in the 2D-IR spectrum, whereas they were poorly-resolved in the IR absorption spectrum is again due to the non-linear nature of the 2D-IR signal. While each mode appearing in the IR absorption spectrum will be visible on the diagonal of the 2D-IR plot, the higher-order dependence of the 2D-IR signal upon the transition dipole moment means that the lineshapes appearing on the diagonal of a 2D-IR spectrum do not exactly match those found in the IR absorption spectrum[31]. Narrower features in the absorption spectrum are exaggerated in the 2D-IR spectrum in relation to broader features[16]. The impact of this on the serum protein spectrum is the appearance of two well-resolved peaks along the diagonal of the 2D-IR plot, where only one broad signal was observed in the IR absorption spectrum.

Figure 4:
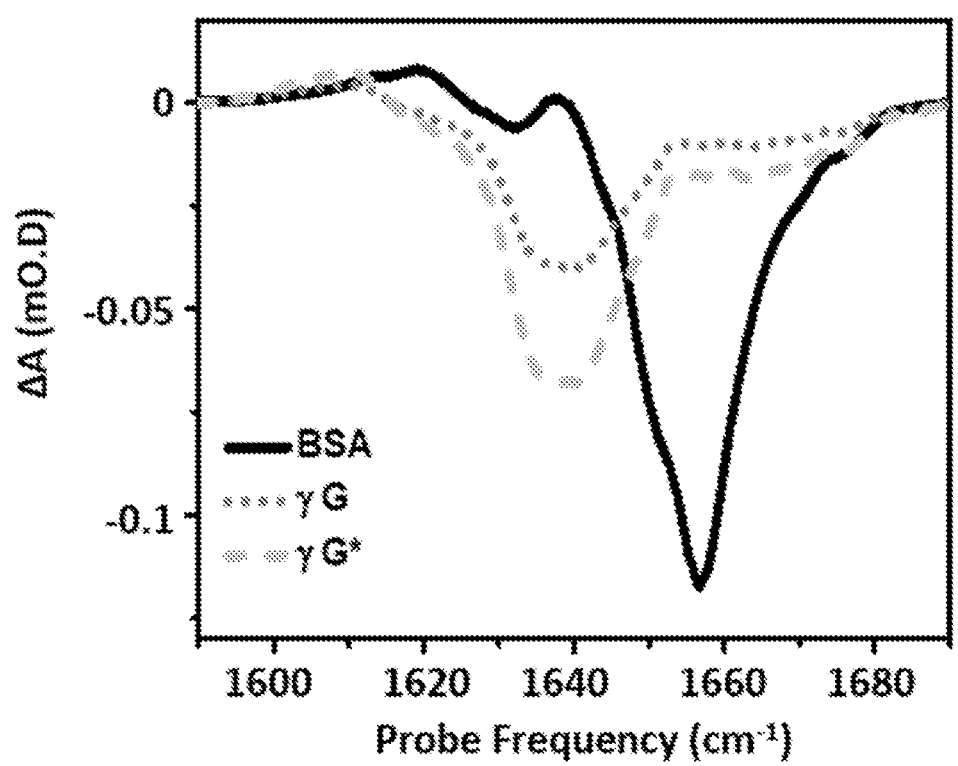
FIG. 4. Diagonal slices through 2D-IR spectra of 50 mg/mL of bovine serum albumin (solid), 30 mg/mL of γ-globulins (bovine) (dotted). Light grey dashed lines shows the slice due to the γ-globulins scaled to reflect a 50 mg/ml concentration.

Based upon the assignment of the two peaks on the 2D-IR spectrum diagonal to albumin and γ-globulins, the relative concentrations of albumin and γ-globulins were quantified. To achieve quantification however, an indication of the relative 2D-IR signal amplitudes of albumin and the γ-globulins is required. This is owing to the fact that serum albumin has a MW of ~66 kDa, while γ-globulins have an average MW of ~150 kDa and the fact that differing secondary structural elements give rise to changes in vibrational coupling of amide I oscillators, which in turn influences the amplitude of the 2D-IR amide I band via the transition dipole moment[16]. The quantitative ratio of the serum albumin and γ-globulin 2D-IR signals were obtained by measurements of known concentrations of the two model proteins under as close as possible to identical conditions (FIG. 4). From the relative maximum amplitudes of the 2D-IR spectrum diagonals of serum albumin and γ-globulins, it was established that, per unit concentration (mg/ml), the albumin signal is 1.8 times larger than the γ-globulin signal. It is noted that, alternatively, a more sophisticated approach could be employed to measure the relative concentrations of albumin to γ-globulins, for example, by using spectrum integrals or lineshape fitting. However, the aim is to provide a fast, straightforward protocol for establishing the AGR avoiding unnecessary data analysis.

Figure 7:
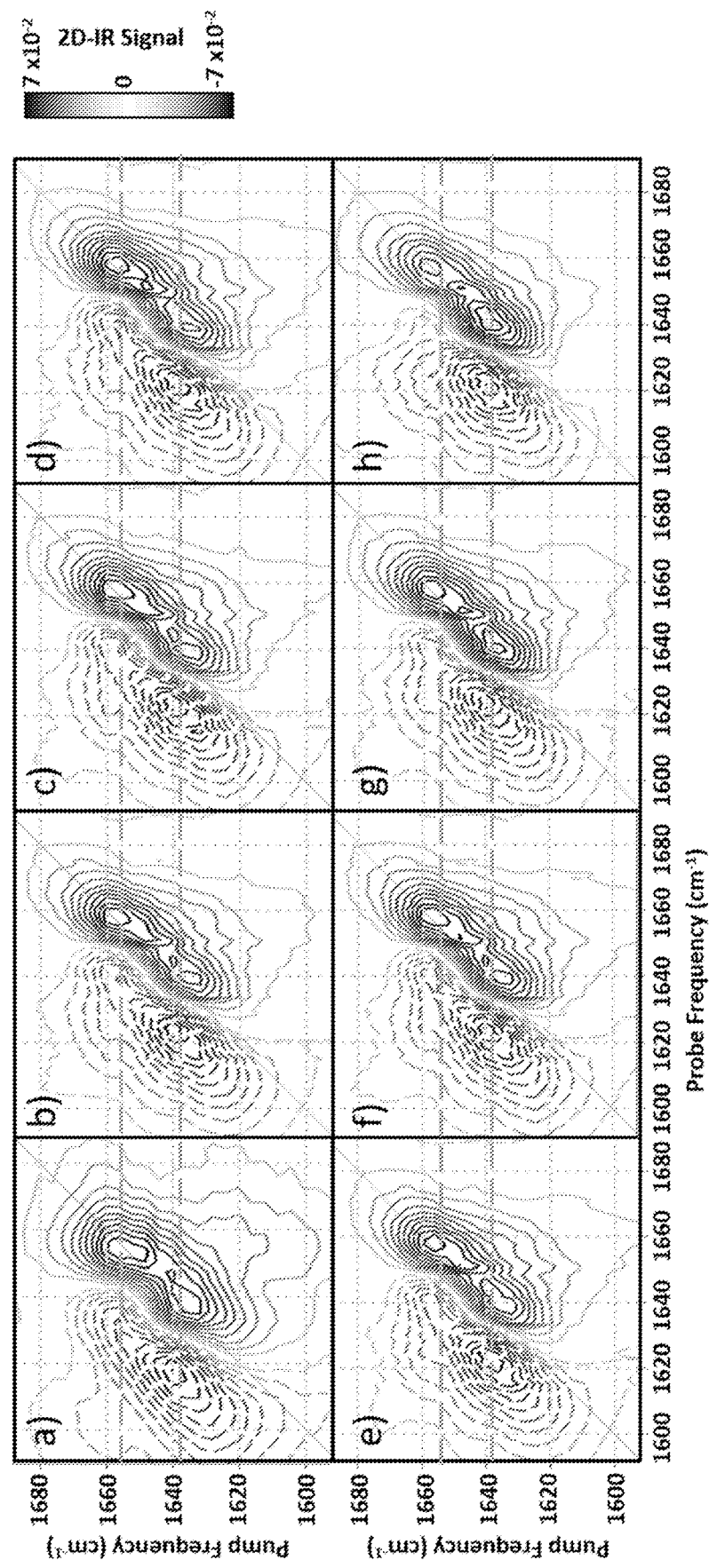
FIG. 7. 2D-IR spectra of the horse serum samples spiked with γ-globulins in the following concentrations (mg/mL): a) 0 b) 0.5 c) 0.9 d) 1.9 e) 3.8 f) 7.5 g) 15 h) 30. Dashed grey horizontal lines show how the peak positions of albumin and γ-globulins discussed in the text. All 2D-IR spectra are plotted on the same scale, negative contours are shown in solid lines and positive contours are dashed.

Applying this amplitude ratio, the AGR of each of the horse serum samples spiked with γ-globulins was established from 2D-IR spectra. The individual 2D-IR spectra are shown in FIG. 7 and the results of the AGR analysis are shown in FIG. 5. Each measurement was made in triplicate and the AGR was extracted using three different methods (see Materials and Methods for details). The first method employed the relative amplitudes of the peaks assigned to albumin and globulins on the 2D-IR spectrum diagonal (FIG. 5(a,b)). The second approach used the amplitudes of the v=0-1 peaks due to albumin and globulins taken from pump-frequency slices through the 2D-IR spectra of the serum samples at 1656 and 1639 cm$^{-1}$ respectively (FIG. 5(c,d)). The third method employed a Single Value Decomposition (SVD) analysis, using a linear combination of the 2D-IR spectra of albumin and γ-globulin model proteins as the basis (FIG. 5(e,f)).

The AGR values were measured from the 2D-IR spectra of the spiked serum samples using these approaches while the variation over triplicate repeat measurements was used to reflect the repeatability of each method (FIG. 5(a,c,e)). These are compared to the real value of the AGR (FIG. 5(a,c,e), solid black line), as determined by traditional analysis of the neat serum sample along with the added γ-globulin spike. The non-spectroscopic AGR measurement of the neat serum was repeated on three individual batches of serum to ensure repeatability.

The results show that all three approaches to determining the AGR from the 2D-IR spectra provide a linear relationship between the determined value of the AGR and the added γ-globulin spike (dashed lines FIG. 5(a,c,e)). As a result, each method is superior to direct IR absorption spectroscopy, which did not produce a reliable value of the AGR, and so the 2D-IR measurements could be used as a calibration curve to determine the AGR value of serum. Of the three 2D-IR methods used, the AGR values derived from the pump slices (FIG. 5(c,d)) were most accurate at the higher values of the AGR, which correspond most closely to the expected human clinical range of 1-2 (the horse serum test samples showed a somewhat lower albumin concentration than is typical for humans). At lower AGR values, the agreement obtained with the pump-slice method was less effective, possibly owing to the very large γ-globulin spike beginning to distort the albumin response. The results obtained from the 2D-IR diagonals was good across the full range of the samples studied (FIG. 5(a,b)), with most 2D-IR-derived values being within the measurement error of the actual AGR value, though a constant offset from the actual AGR value was noted. This is thought to be caused by different anharmonicities of the proteins resulting in a diagonal line that does not run exactly through the centre of each 2D-IR peak and this could also easily be corrected in an AGR calibration plot. Finally, the SVD approach yielded excellent agreement over the mid-range of the spiked samples (AGR=0.5-0.7), but was less effective at the extremities.

Figures 5A, 5B, 5C, 5D, 5E, 5F, 5G:
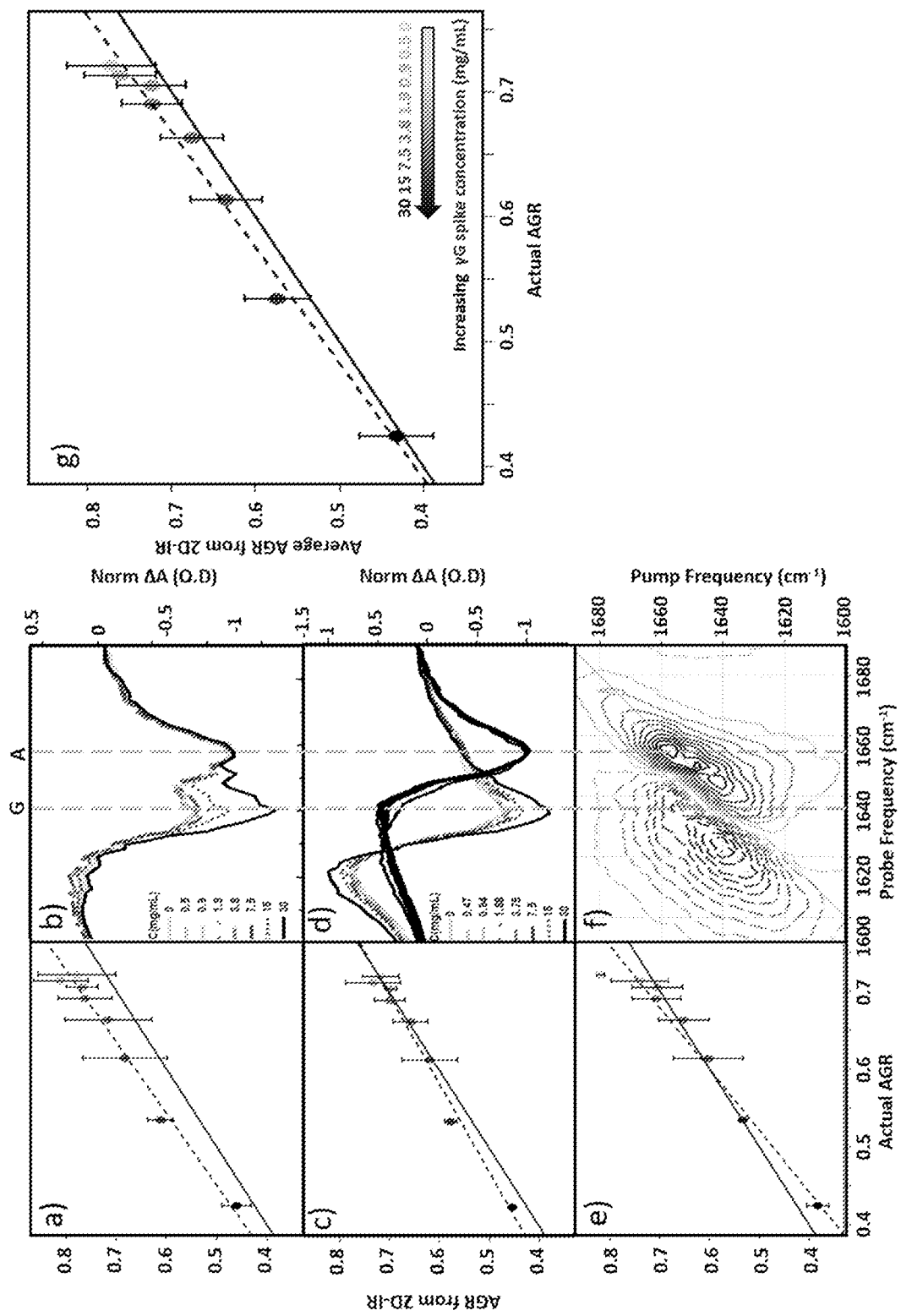
FIG. 5. Results of determining the AGR of the horse serum samples spiked with γ-globulins from 2D-IR spectroscopy. a) AGR values obtained using the 2D-IR diagonal method (see text). The spectral basis of the method is shown in b), which shows the variation in the 2D-IR diagonal with γ-globulin spike. c) AGR values obtained using the pump slice method (see text). The spectral basis of the method is shown in d) where coloured traces show the pump slice through the γ-globulin signal (1639 cm$^{-1}$) at different levels of γ-globulin spike, the black traces show the corresponding slice through the albumin peak at 1656 cm$^{-1}$. e) AGR values obtained using the 2D-IR SVD method (see text). The results of a typical SVD analysis is shown in f). g) AGR values obtained from averaging the results shown in panels a), c) and e). In panels a), c), e) and g) the solid black line indicates the actual AGR of the samples. Error bars show 2a variation. Dashed lines show linear fits to the experimental AGR values.
Figure 8:
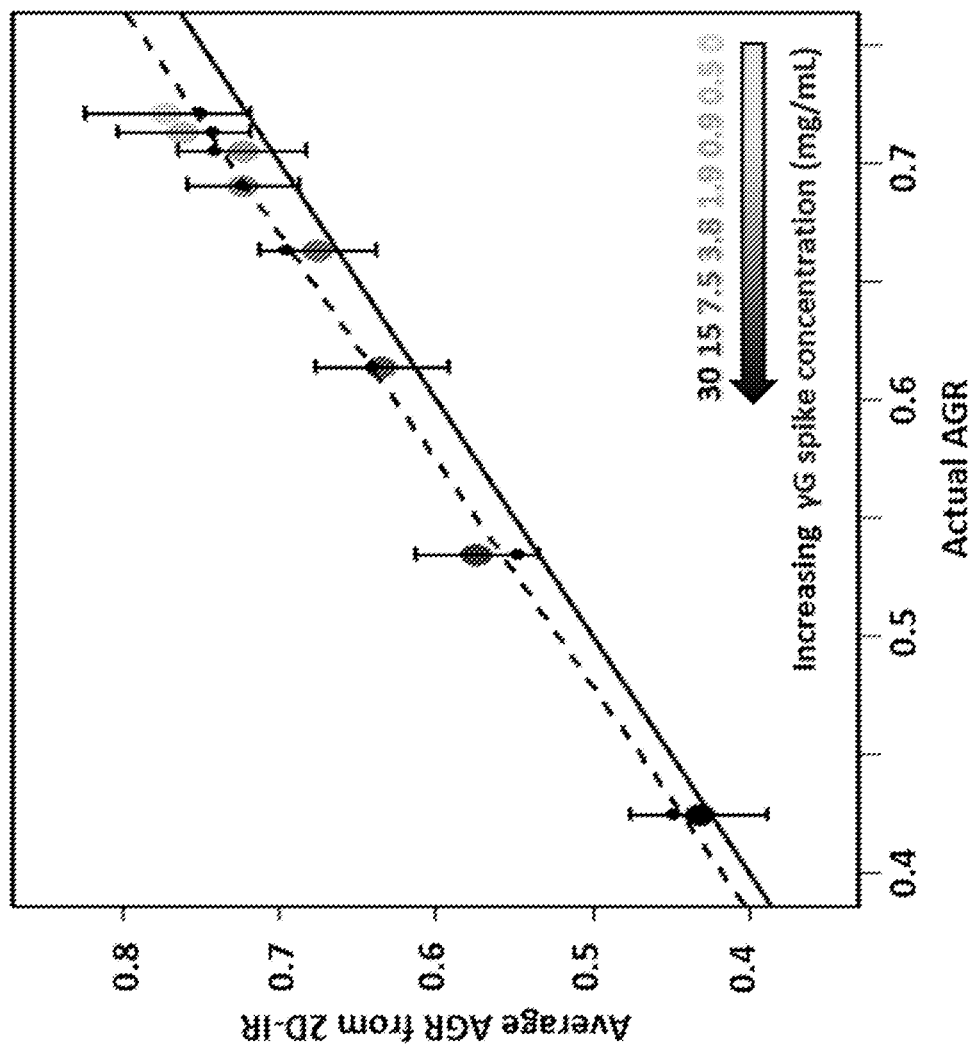
FIG. 8. Results of leave one out-type tests. Every data point (comprised of the average of the three analysis methods on the average of three measurements) is left out in turn and the linear fit is recalculated. The AGR is then predicted for each data point using the actual AGR and the linear model, as shown by the solid black dots. The solid black line indicates the actual AGR of the samples. Error bars show 2a variation. The dashed line shows a linear fit to the experimental AGR values for the horse serum samples spiked with γ-globulins.

Taking an average of the three analysis approaches (FIG. 5(g)) produced agreement with actual AGR values across the full range of samples, within the experimental uncertainty. It is noted however that, in the interests of minimising data analysis, the pump-slice approach is extremely accurate at realistic values of the AGR. In order to test the accuracy of the method, we performed both blind tests, using samples of unknown concentration and leave one out-type tests of the analysis protocol. In all cases the results showed accuracy to within the expected error of the measurement (FIG. 8). Overall, although the AGR values present in our horse serum model are a little lower than those found in humans, it is clear that the 2D-IR measurements tested here will show accuracy over a clinically-relevant range.

Based upon comparisons with the actual AGR values of the samples, the estimated accuracy of the 2D-IR-derived AGR measurement is ±0.03 (~4%). Direct comparisons with the current wet assay technique are not possible because these tests derive the AGR value from the difference in total protein and albumin concentrations, however typical quoted accuracies are in the μg/ml range.

Figures 6A, 6B, 6C, 6D, 6E, 6F, 6G, 6H:
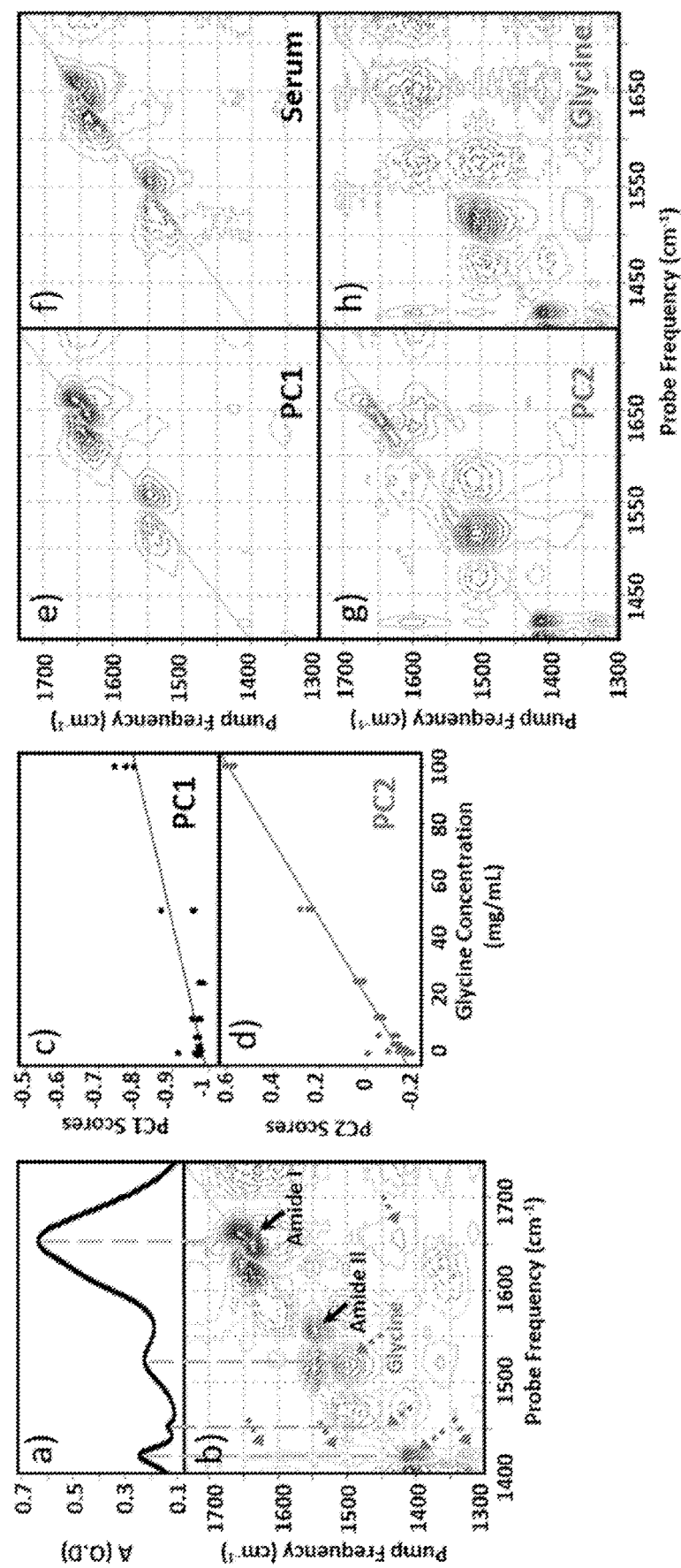
FIG. 6. (a) IR absorption spectrum of serum spiked with 100 mg/ml glycine. (b) shows a 2D-IR spectrum of the same sample. Solid black arrows identify diagonal peaks due to proteins. Dashed grey arrows identify the unique 2D peak pattern of glycine. c)-h) Results of carrying out Principal Component Analysis on a range of glycine-spiked serum samples shows separation of the serum and glycine spectral responses into PC1 and PC2 respectively. c) PC1 scores as a function of glycine concentration d) PC2 scores as a function of glycine concentration. e) PC1 loading plot alongside the experimentally-derived serum spectrum (f). g) PC2 loading plot, alongside the experimentally-derived glycine spectrum h). All 2D-IR spectra are plotted on the same scale, negative contours are shown in solid lines and positive contours are dashed.

2D-IR spectroscopy may also be useful in detecting lower molecular weight biomarkers in serum samples. Typical examples are lipids, peptides[32-34], sugars or nucleic acids[35-43]. To demonstrate the approach, serum samples were spiked with glycine. FIG. 6(b) shows a 2D-IR spectrum of serum spiked with 100 mg/ml glycine alongside the IR absorption spectrum (FIG. 6(a)). The example shown contains a high concentration of glycine to show the spectral features clearly but additions as low as 0.25 mg/ml were studied. Peaks due to glycine are visible in the IR absorption spectrum (FIG. 6(a)), generally occurring to lower frequencies than the amide I and II bands of the protein. However, some element of spectral overlap does occur near 1550 cm$^{-1}$ and near the protein amide I peak (1650 cm$^{-1}$). Any uncertainty caused by this overlap is removed in the 2D-IR spectrum (FIG. 6(b)). Here, the bands due to the protein (black arrows) and glycine (dotted arrows) are well-separated, while the off-diagonal peaks linking the coupled vibrational modes of glycine create a unique 2D pattern that can be used to definitively identify the glycine contribution. These features are clearly resolvable in aqueous serum and so circumvent any effects due to overlap of spectral contributions from other aspects of the mixture that lie on the diagonal of the spectrum. To demonstrate the ability of 2D-IR spectroscopy to separate protein and low-molecular weight fractions, Principal Component Analysis (PCA) was applied to 2D-IR spectra of a set of serum samples spiked with differing glycine concentrations (FIG. 6 (c-h)). The results show that the PC1 score was largely invariant across the sample set (FIG. 6(c)) and the associated PC1 spectrum (FIG. 6(e)) was in excellent agreement with that of neat serum (FIG. 6(f)). The invariance of PC1 with glycine concentration was lost slightly at very high glycine concentrations, possibly due to the presence of a weak glycine band occurring near 1650 cm$^{-1}$. In contrast to the invariance of PC1, the PC2 scores showed a linear correlation with glycine concentration (FIG. 6(d)) and the associated PC2 spectral density (FIG. 6(g)) is in excellent agreement with the spectrum of glycine itself (FIG. 6(h)). Thus, 2D-IR is able to spectrally separate and quantify low molecular weight fractions. This example gives an indication of how 2D-IR might be used to quantify the presence of small molecules or species such as sugars, nucleic acids or lipids in biofluids.

Overall, these experiments show that the method of the invention using 2D-IR offers a simple, robust approach to determining the AGR of serum using a single spectroscopic measurement without the need for time consuming sample or data analysis. The ability to use the 2D-IR experiment to suppress the water background signal enables data collection in simple transmission mode and so circumvents the impact of potential spectral artefacts from alternative detection strategies. It is believed that this is the first label-free optical measurement of the AGR.

As used herein, the term "comprising", which is inclusive or open-ended and does not exclude additional unrecited elements or method steps, is intended to encompass as alternative embodiments, the phrases "consisting essentially of" and "consisting of" where "consisting of" excludes any element or step not specified and "consisting essentially of" permits the inclusion of additional unrecited elements or steps that do not materially affect the essential or basic and novel characteristics of the composition or method under consideration.

REFERENCES

1. Hu, S.; Loo, J. A.; Wong, D. T., Human body fluid proteome analysis. *Proteomics* 2006, 6 (23), 6326-6353.
2. Petricoin, E. F.; Belluco, C.; Araujo, R. P.; Liotta, L. A., The blood peptidome: a higher dimension of information content for cancer biomarker discovery. *Nature Reviews Cancer* 2006, 6 (12), 961-967.
3. Baker, M. J.; Hussain, S. R.; Lovergne, L.; Untereiner, V.; Hughes, C.; Lukaszewski, R. A.; Thiefin, G.; Sockalingum, G. D., Developing and understanding biofluid vibrational spectroscopy: a critical review. *Chem Soc Rev* 2016, 45 (7), 1803-1818.
4. Grosserueschkamp, F.; Bracht, T.; Diehl, H. C.; Kuepper, C.; Ahrens, M.; Kallenbach-Thieltges, A.; Mosig, A.; Eisenacher, M.; Marcus, K.; Behrens, T.; Bruning, T.; Theegarten, D.; Sitek, B.; Gerwert, K., Spatial and molecular resolution of diffuse malignant mesothelioma heterogeneity by integrating label-free FTIR imaging, laser capture microdissection and proteomics. *Scientific Reports* 2017, 7.
5. Koyama, T.; Kuriyama, N.; Ozaki, E.; Matsui, D.; Watanabe, I.; Miyatani, F.; Kondo, M.; Tamura, A.; Kasai, T.; Ohshima, Y.; Yoshida, T.; Tokuda, T.; Mizuta, I.; Mizuno, S.; Yamada, K.; Takeda, K.; Matsumoto, S.;

Nakagawa, M.; Mizuno, T.; Watanabe, Y., Serum albumin to globulin ratio is related to cognitive decline via reflection of homeostasis: a nested case-control study. *Bmc Neurology* 2016, 16.

6. Peters, A. S.; Backhaus, J.; Pfutzner, A.; Raster, M.; Burgard, G.; Demirel, S.; Bockler, D.; Hakimi, M., Serum-infrared spectroscopy is suitable for diagnosis of atherosclerosis and its clinical manifestations. *Vibrational Spectroscopy* 2017, 92, 20-26.

7. Liu, J. J.; Chen, S. X.; Geng, Q. R.; Liu, X. C.; Kong, P. F.; Zhan, Y. Q.; Xu, D. Z., Prognostic value of pretreatment albumin-globulin ratio in predicting long-term mortality in gastric cancer patients who underwent D2 resection. *Oncotargets and Therapy* 2017, 10, 2155-2162.

8. Putnam, F. W., *The plasma proteins 2nd Edition*. AP London: 1975; Vol. 1.

9. Hands, J. R.; Dorling, K. M.; Abel, P.; Ashton, K. M.; Brodbelt, A.; Davis, C.; Dawson, T.; Jenkinson, M. D.; Lea, R. W.; Walker, C.; Baker, M. J., Attenuated Total Reflection Fourier Transform Infrared (ATR-FTIR) spectral discrimination of brain tumour severity from serum samples. *Journal of Biophotonics* 2014, 7 (3-4), 189-199.

10. Gajjar, K.; Trevisan, J.; Owens, G.; Keating, P. J.; Wood, N. J.; Stringfellow, H. F.; Martin-Hirsch, P. L.; Martin, F. L., Fourier-transform infrared spectroscopy coupled with a classification machine for the analysis of blood plasma or serum: a novel diagnostic approach for ovarian cancer. *Analyst* 2013, 138 (14), 3917-3926.

11. Bonnier, F.; Petitjean, F.; Baker, M. J.; Byrne, H. J., Improved protocols for vibrational spectroscopic analysis of body fluids. *Journal of Biophotonics* 2014, 7 (3-4), 167-179.

12. Hughes, C.; Clemens, G.; Bird, B.; Dawson, T.; Ashton, K. M.; Jenkinson, M. D.; Brodbelt, A.; Weida, M.; Fotheringham, E.; Barre, M.; Rowlette, J.; Baker, M. J., Introducing Discrete Frequency Infrared Technology for High-Throughput Biofluid Screening. *Scientific Reports* 2016, 6.

13. Kong, K.; Kendall, C.; Stone, N.; Notingher, I., Raman spectroscopy for medical diagnostics—From in-vitro biofluid assays to in-vivo cancer detection. *Advanced Drug Delivery Reviews* 2015, 89, 121-134.

14. Baiz, C. R.; Peng, C. S.; Reppert, M. E.; Jones, K. C.; Tokmakoff, A., Coherent two-dimensional infrared spectroscopy: Quantitative analysis of protein secondary structure in solution. *Analyst* 2012, 137 (8), 1793-1799.

15. Minnes, L.; Shaw, D. J.; Cossins, B.; Donaldson, P. M.; Greetham, G. M.; Towrie, M.; Parker, A. W.; Baker, M. J.; Henry, A.; Taylor, R.; Hunt, N. T., Quantifying Secondary Structure Changes in Calmodulin using 2D-IR Spectroscopy. *Analytical Chemistry* 2017, 89 10898-10906.

16. Dunkelberger, E. B.; Grechko, M.; Zanni, M. T., Transition Dipoles from 1D and 2D Infrared Spectroscopy Help Reveal the Secondary Structures of Proteins: Application to Amyloids. *J Phys Chem B* 2015, 119 (44), 14065-14075.

17. Shaw, D. J.; Hill, R. E.; Simpson, N.; Husseini, F. S.; Robb, K.; Greetham, G. M.; Towrie, M.; Parker, A. W.; Robinson, D.; Hirst, J. D.; Hoskisson, P. A.; Hunt, N. T., Examining the role of protein structural dynamics in drug resistance in *Mycobacterium tuberculosis Chemical Science* 2017, 8, 8384-8399.

18. Singh, V.; Peng, C. S.; Li, D. Y.; Mitra, K.; Silvestre, K. J.; Tokmakoff, A.; Essigmann, J. M., Direct Observation of Multiple Tautomers of Oxythiamine and their Recognition by the Thiamine Pyrophosphate Riboswitch. *ACS Chem Biol* 2014, 9 (1), 227-236.

19. Ishikawa, H.; Finkelstein, I. J.; Kim, S.; Kwak, K.; Chung, J. K.; Wakasugi, K.; Massari, A. M.; Fayer, M. D., Neuroglobin dynamics observed with ultrafast 2D-IR vibrational echo spectroscopy. *Proc Nat Acad Sci* 2007, 104, 16116-16121.

20. Shim, S. H.; Strasfeld, D. B.; Ling, Y. L.; Zanni, M. T., Automated 2D-IR Spectroscopy Using a Mid-IR Pulse Shaper and Application of this Technology to the Human Islet Amyloid Polypeptide. *Proc Nat Acad Sci* 2007, 104 (36), 14197-14202.

21. Donaldson, P. M.; Greetham, G. M.; Shaw, D. J.; Parker, A. W.; Towrie, M., A 100 kHz Pulse Shaping 2D-IR Spectrometer Based on Dual Yb:KGW Amplifiers. *J Phys Chem A* 2018, 122 (3), 780-787.

22. Tracy, K. M.; Barich, M. V.; Carver, C. L.; Luther, B. M.; Krummel, A. T., High-Throughput Two-Dimensional Infrared (2D-IR) Spectroscopy Achieved by Interfacing. Microfluidic Technology with a High Repetition Rate 2D-IR Spectrometer. *Journal of Physical Chemistry Letters* 2016, 7 (23), 4865-4870.

23. Luther, B. M.; Tracy, K. M.; Gerrity, M.; Brown, S.; Krummel, A. T., 2D IR spectroscopy at 100 kHz utilizing a Mid-IR OPCPA laser source. *Optics Express* 2016, 24 (4), 4117-4127.

24. Fritzsch, R.; Donaldson, P. M.; Greetham, G. M.; Towrie, M.; Parker, A. W.; Baker, M. J.; Hunt, N. T., Rapid screening of DNA-ligand complexes via 2D-IR spectroscopy and ANOVA-PCA *Analytical Chemistry* 2018, doi: 10.1021/acs.analchem.7b04727.

25. Paarmann, A.; Hayashi, T.; Mukamel, S.; Miller, R. J. D., Probing intermolecular couplings in liquid water with two-dimensional infrared photon echo spectroscopy. *J Chem Phys* 2008, 128 (19).

26. Kraemer, D.; Cowan, M. L.; Paarmann, A.; Huse, N.; Nibbering, E. T. J.; Elsaesser, T.; Miller, R. J. D., Temperature dependence of the two-dimensional infrared spectrum of liquid H2O. *Proc Nat Acad Sci* 2008, 105 (2), 437-442.

27. Dahms, F.; Fingerhut, B. P.; Nibbering, E. T. J.; Pines, E.; Elsaesser, T., Large-amplitude transfer motion of hydrated excess protons mapped by ultrafast 2D IR spectroscopy. *Science* 2017, 357 (6350), 491-494.

28. De Marco, L.; Fournier, J. A.; Thamer, M.; Carpenter, W.; Tokmakoff, A., Anharmonic exciton dynamics and energy dissipation in liquid water from two-dimensional infrared spectroscopy. *J Chem Phys* 2016, 145 (9).

29. Thamer, M.; De Marco, L.; Ramasesha, K.; Mandal, A.; Tokmakoff, A., Ultrafast 2D-IR spectroscopy of the excess proton in liquid water. *Science* 2015, 350 (6256), 78-82.

30. Huse, N.; Ashihara, S.; Nibbering, E. T. J.; Elsaesser, T., Vibrational couplings and ultrafast relaxation of the O—H bending mode in liquid H2O. *Chem Phys Lett* 2005, 404, 389.

31. Hamm, P.; Zanni, M. T., *Concepts and Method of 2D Infrared Spectroscopy*. Cambridge University Press: Cambridge, 2011.

32. Kim, Y. S.; Wang, J. P.; Hochstrasser, R. M., Two-dimensional infrared spectroscopy of the alanine dipeptide in aqueous solution. *J Phys Chem B* 2005, 109 (15), 7511-7521.

33. Kim, Y. S.; Hochstrasser, R. M., Dynamics of amide-I modes of the alanine dipeptide in D2O. *J Phys Chem B* 2005, 109 (14), 6884-6891.

34. Zanni, M. T.; Stenger, J.; Asplund, M. C.; Hochstrasser, R. M., Solvent dependent conformational dynamics of dipeptides studied with two-dimensional infrared spectroscopy. *Biophys J* 2001, 80 (1), 8A-9A.

35. Ramakers, L. A. I.; Hithell, G.; May, J. J.; Greetham, G. M.; Donaldson, P. M.; Towrie, M.; Parker, A. W.; Burley, G. A.; Hunt, N. T., 2D-IR spectroscopy shows that optimized DNA minor groove binding of Hoechst33258 follows an induced fit model. *J. Phys. Chem. B* 2017, 121, 1295-1303.

36. Hithell, G.; Ramakers, L. A. I.; Burley, G. A.; Hunt, N. T., Applications of 2D-IR spectroscopy to probe the structural dynamics of DNA. In *Frontiers in Molecular Spectroscopy*, Laane, J., Ed. Elsevier: 2017; p in press.

37. Hithell, G.; Gonzalez-Jimenez, M.; Greetham, G. M.; Donaldson, P. M.; Towrie, M.; Parker, A. W.; Burley, G. A.; Wynne, K.; Hunt, N. T., Ultrafast 2D-IR and optical Kerr effect spectroscopy reveal the impact of duplex melting on the structural dynamics of DNA. *Phys Chem Chem Phys* 2017, 19 (16), 10333-10342.

38. Greve, C.; Preketes, N. K.; Fidder, H.; Costard, R.; Koeppe, B.; Heisler, I. A.; Mukamel, S.; Temps, F.; Nibbering, E. T. J.; Elsaesser, T., N—H Stretching Excitations in Adenosine-Thymidine Base Pairs in Solution: Pair Geometries, Infrared Line Shapes, and Ultrafast Vibrational Dynamics. *J Phys Chem A* 2013, 117 (3), 594-606.

39. Yang, M.; Szyc, L.; Elsaesser, T., Femtosecond Two-Dimensional Infrared Spectroscopy of Adenine-Thymine Base Pairs in DNA Oligomers. *J Phys Chem B* 2011, 115 (5), 1262-1267.

40. Szyc, L.; Dwyer, J. R.; Nibbering, E. T. J.; Elsaesser, T., Ultrafast dynamics of N—H and O—H stretching excitations in hydrated DNA oligomers. *Chem Phys* 2009, 357 (1-3), 36-44.

41. Krummel, A. T.; Zanni, M. T., DNA vibrational coupling revealed with two-dimensional infrared spectroscopy: Insight into why vibrational spectroscopy is sensitive to DNA structure. *J Phys Chem B* 2006, 110 (28), 13991-14000.

42. Krummel, A. T.; Mukherjee, P.; Zanni, M. T., Inter and intrastrand vibrational coupling in DNA studied with heterodyned 2D-IR spectroscopy. *J Phys Chem B* 2003, 107, 9165-9169.

43. Peng, C. S.; Jones, K. C.; Tokmakoff, A., Anharmonic Vibrational Modes of Nucleic Acid Bases Revealed by 2D IR Spectroscopy. *J Am Chem Soc* 2011, 133 (39), 15650-15660.

44. Adamczyk, K.; Candelaresi, M.; Kania, R.; Robb, K.; Bellota-Anton, C.; Greetham, G. M.; Pollard, M. R.; Towrie, M.; Parker, A. W.; Hoskisson, P. A.; Tucker, N. P.; Hunt, N. T., The Effect of Point Mutation on the Protein—Ligand Interactions in Equilibrium Structural Fluctuations of Myoglobin *Phys Chem Chem Phys* 2012, 14, 7411-7419.

45. Greetham, G. M.; Burgos, P.; Cao, Q.; Clark, I. P.; Codd, P. S.; Farrow, R. C.; George, M. W.; Kogimtzis, M.; Matousek, P.; Parker, A. W.; Pollard, M. R.; Robinson, D. A.; Xin, Z.-J.; Towrie, M., ULTRA: A Unique Instrument for Time-Resolved Spectroscopy. *Appl. Spectrosc* 2010, 64, 1311-1319.

46. R Development Core Team *R: A language and environment for statistical computing*, R Foundation for Statistical Computing. Vienna, Austria: 2010.

The invention claimed is:

1. A method of analyzing an aqueous fluid, said method comprising:
    obtaining a 2D-IR spectrum of a sample of the aqueous fluid using a 2D-IR spectrometer configured to apply a sequence of IR pulses to the sample, and
    determining whether or not one or more proteins are present in the aqueous fluid by observing the amide I band of the one or more proteins,
    wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs.

2. The method according to claim 1, wherein the pump process is a sequence of a first pump pulse and a second pump pulse and $T_w$ is time between applying the second pump pulse and applying the probe pulse.

3. The method according to claim 2, wherein $T_w$ is from 200 to 300 fs.

4. The method according to claim 1, wherein $T_w$ is from 200 to 300 fs.

5. The method according to claim 1, further comprising identifying at least one peak by comparing the 2D-IR spectrum with one or more reference 2D-IR spectra.

6. The method according to claim 1, further comprising determining whether or not albumin is present in the aqueous fluid by determining if the spectrum has a peak at a frequency of 1656 $cm^{-1}$ and/or determining if γ-globulins are present in the aqueous fluid by determining if the spectrum has a peak at a frequency of 1639 $cm^{-1}$.

7. The method according to claim 1, further comprising identifying at least one peak and quantifying the at least one peak using a calibration based on one or more reference 2D-IR spectra.

8. The method according to claim 1, wherein the 2D-IR spectrum comprises peaks due to albumin and globulins and the method comprises determining a ratio of albumin to globulins present in the sample.

9. The method according to claim 1, wherein the 2D-IR spectrum comprises a peak due to albumin and a peak due to γ-globulins and the method comprises determining a ratio of albumin to γ-globulins by measuring a peak height of the albumin peak and a peak height of the γ-globulins peak and dividing the peak height of the albumin peak by the peak height of the γ-globulins peak multiplied by 1.8.

10. The method of diagnosing and/or prognosing an abnormality in a subject comprising analyzing a sample of an aqueous biofluid from the subject using the method of claim 9.

11. A method according to claim 10, wherein the method comprises determining from the 2D-IR spectrum whether treatment of the subject or further testing of the subject is required.

12. A method according to claim 10, wherein the abnormality is poor general health or the presence of an inflammatory response, and the method involves determining the ratio of albumins to γ-globulins in the aqueous biofluid.

13. A method according to claim 10, wherein the 2D-IR spectrum is compared to a plurality of pre-correlated spectra stored in a database in order to derive a correlation with a favorable or unfavorable diagnosis or wherein the spectrum is correlated with a favorable or unfavorable diagnosis based on a predictive model developed by "training" a database of pre-correlated analyses.

14. The method according to claim 1, wherein the aqueous fluid is an aqueous biofluid.

15. The method according to claim 14, wherein the method comprises obtaining a sample of the aqueous biofluid from the subject.

16. A method according to claim 15, wherein the method comprises determining from the 2D-IR spectrum whether treatment of the subject or further testing of the subject is required.

17. A method according to claim 15, wherein the abnormality is poor general health or the presence of an inflammatory response, and the method involves determining the ratio of albumins to γ-globulins in the aqueous biofluid.

18. A method according to claim 17, wherein the 2D-IR spectrum is compared to a plurality of pre-correlated spectra stored in a database in order to derive a correlation with a favorable or unfavorable diagnosis or wherein the spectrum is correlated with a favorable or unfavorable diagnosis based on a predictive model developed by "training" a database of pre-correlated analyses.

19. A method of analyzing an aqueous fluid, said method comprising:
    obtaining a 2D-IR spectrum of a sample of the aqueous fluid using a 2D-IR spectrometer configured to apply a sequence of IR pulses to the sample, the 2D-IR spectrum including peaks due to albumin and globulins, and
    determining a ratio of albumin to globulins present in the sample,
    wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs.

20. A method of analyzing an aqueous fluid, said method comprising:
    obtaining a 2D-IR spectrum of a sample of the aqueous fluid using a 2D-IR spectrometer configured to apply a sequence of IR pulses to the sample, the 2D-IR spectrum including a peak due to albumin and a peak due to γ-globulins, and
    determining a ratio of albumin to γ-globulins by measuring a peak height of the albumin peak and a peak height of the γ-globulins peak and dividing the peak height of the albumin peak by the peak height of the γ-globulins peak multiplied by 1.8,
    wherein the sequence comprises a pump process followed by a probe pulse, where the pump process is a single pump pulse or a sequence of a first pump pulse and a second pump pulse, and a waiting time $T_w$ between applying the single pump pulse or the second pump pulse and applying the probe pulse is from 150 to 350 fs.

\* \* \* \* \*